US012806419B2

(12) United States Patent
Libbus et al.

(10) Patent No.: US 12,806,419 B2
(45) Date of Patent: Nov. 24, 2026

(54) EVALUATION OF VAGUS NERVE STIMULATION USING HEART RATE VARIABILITY ANALYSIS

(71) Applicant: LivaNova USA, Inc., Houston, TX (US)

(72) Inventors: Imad Libbus, St. Paul, MN (US); Bruce D. Nearing, North Reading, MA (US); Badri Amurthur, Los Gatos, CA (US); Bruce H. KenKnight, Maple, MN (US); Richard L. Verrier, Dennis, MA (US)

(73) Assignee: LivaNova USA, Inc., Houston, TX (US)

( * ) Notice: Subject to any disclaimer, the term of this patent is extended or adjusted under 35 U.S.C. 154(b) by 0 days.

(21) Appl. No.: 18/663,956

(22) Filed: May 14, 2024

(65) Prior Publication Data

US 2024/0382755 A1 Nov. 21, 2024

Related U.S. Application Data

(63) Continuation of application No. 18/092,716, filed on Jan. 3, 2023, now Pat. No. 11,980,758, which is a (Continued)

(51) Int. Cl.

*A61N 1/36* (2006.01)
*A61B 5/024* (2006.01)

(Continued)

(52) U.S. Cl.

CPC ...... *A61N 1/36114* (2013.01); *A61B 5/02405* (2013.01); *A61N 1/36139* (2013.01);

(Continued)

(58) Field of Classification Search

CPC ............ A61N 1/36114; A61N 1/36139; A61N 1/3616; A61N 1/36175; A61N 1/36196;

(Continued)

(56) References Cited

U.S. PATENT DOCUMENTS

| | | | |
|---|---|---|---|
| 5,285,793 | A | 2/1994 | Slovut et al. |
| 11,554,263 | B2 | 1/2023 | Libbus et al. |

(Continued)

OTHER PUBLICATIONS

Libbus et al., "Quantitative Evaluation of Heartbeat Interval Time Series Using Poincare Analysis Reveals Distinct Patterns of Heart Rate Dynamics During Cycles of Vagus Nerve Stimulation in Patients with Heart Failure," Journal of Electrocardiology, vol. 50, 2017 (pp. 898-903).

*Primary Examiner* — Niketa Patel
*Assistant Examiner* — Sebastian X Lukjan
(74) *Attorney, Agent, or Firm* — Foley & Lardner LLP

(57) ABSTRACT

An implantable vagus nerve stimulation (VNS) system includes a sensor configured to measure ECG data for a patient, a stimulation subsystem configured to deliver VNS to the patient, and a control system configured to perform a heart rate variability analysis with the ECG data. In some aspects, performing the heart rate variability analysis includes measuring R-R intervals between successive R-waves for the ECG data measured during a stimulation period of VNS therapy and a baseline period of the VNS therapy, wherein the stimulation period comprises at least a portion of the ON period and the baseline period comprises at least a portion of the OFF period immediately preceding the ON period, and generating a plot of each R-R interval against an immediately successive R-R interval for each of the stimulation period and the baseline period configured to be displayed on a display.

20 Claims, 9 Drawing Sheets

Related U.S. Application Data continuation of application No. 16/422,746, filed on May 24, 2019, now Pat. No. 11,554,263.

(60) Provisional application No. 62/676,883, filed on May 25, 2018.

(51) Int. Cl.
*A61B 5/352* (2021.01)
*A61B 5/366* (2021.01)

(52) U.S. Cl.
CPC ............... *A61B 5/352* (2021.01); *A61B 5/366* (2021.01); *A61N 1/3616* (2013.01); *A61N 1/36175* (2013.01); *A61N 1/36196* (2013.01)

(58) Field of Classification Search
CPC ............ A61N 1/36171; A61B 5/20405; A61B 5/352; A61B 5/366; A61B 5/4836
See application file for complete search history.

(56) References Cited

U.S. PATENT DOCUMENTS

| | | | | |
|---|---|---|---|---|
| 2008/0015659 | A1 | 1/2008 | Zhang et al. | |
| 2008/0091240 | A1* | 4/2008 | Ben-David ........ | A61N 1/36114 607/4 |
| 2009/0292180 | A1 | 11/2009 | Mirow | |
| 2009/0326401 | A1 | 12/2009 | Jonckheere et al. | |
| 2014/0228912 | A1* | 8/2014 | Seim .................. | A61N 1/37247 607/59 |
| 2014/0236261 | A1* | 8/2014 | Ternes ............... | A61N 1/37264 607/59 |
| 2014/0364921 | A1 | 12/2014 | Legay et al. | |
| 2015/0141851 | A1 | 5/2015 | Sharma | |
| 2016/0038754 | A1 | 2/2016 | Adjouadi et al. | |
| 2017/0203103 | A1* | 7/2017 | Levine ................. | A61B 5/4836 |
| 2017/0325733 | A1 | 11/2017 | Hettrick et al. | |
| 2017/0361097 | A1* | 12/2017 | Williamson ....... | A61N 1/36025 |

* cited by examiner

EVALUATION OF VAGUS NERVE STIMULATION USING HEART RATE VARIABILITY ANALYSIS

CROSS REFERENCE TO RELATED PATENT APPLICATION

This application is a continuation of U.S. patent application Ser. No. 18/092,716, entitled “EVALUATION OF VAGUS NERVE STIMULATION USING HEART RATE VARIABILITY ANALYSIS,” filed Jan. 3, 2023, which is a continuation of U.S. patent application Ser. No. 16/422,746, entitled “EVALUATION OF VAGUS NERVE STIMULATION USING HEART RATE VARIABILITY ANALYSIS,” filed May 24, 2019, which claims priority to U.S. Provisional Patent Application No. 62/676,883, entitled “EVALUATION OF VAGUS NERVE STIMULATION USING HEART RATE VARIABILITY ANALYSIS,” filed May 25, 2018, each of which is incorporated herein by reference in its entirety.

BACKGROUND

The present disclosure relates generally to neurostimulation and, more specifically, to improved systems and methods for managing titration of stimulation.

Chronic heart failure (CHF) and other forms of chronic cardiac dysfunction (CCD) may be related to an autonomic imbalance of the sympathetic and parasympathetic nervous systems that, if left untreated, can lead to cardiac arrhythmogenesis, progressively worsening cardiac function and eventual patient death. CHF is pathologically characterized by an elevated neuroexcitatory state and is accompanied by physiological indications of impaired arterial and cardiopulmonary baroreflex function with reduced vagal activity.

CHF triggers compensatory activations of the sympathoadrenal (sympathetic) nervous system and the renin-angiotensin-aldosterone hormonal system, which initially helps to compensate for deteriorating heart-pumping function, yet, over time, can promote progressive left ventricular dysfunction and deleterious cardiac remodeling. Patients suffering from CHF are at increased risk of tachyarrhythmias, such as atrial fibrillation (AF), ventricular tachyarrhythmias (ventricular tachycardia (VT) and ventricular fibrillation (VF)), and atrial flutter, particularly when the underlying morbidity is a form of coronary artery disease, cardiomyopathy, mitral valve prolapse, or other valvular heart disease. Sympathoadrenal activation also significantly increases the risk and severity of tachyarrhythmias due to neuronal action of the sympathetic nerve fibers in, on, or around the heart and through the release of epinephrine (adrenaline), which can exacerbate an already-elevated heart rate.

The standard of care for managing CCD in general continues to evolve. For instance, new therapeutic approaches that employ electrical stimulation of neural structures that directly address the underlying cardiac autonomic nervous system imbalance and dysregulation have been proposed. In one form, controlled stimulation of the cervical vagus nerve beneficially modulates cardiovascular regulatory function. Vagus nerve stimulation (VNS) has been used for the clinical treatment of drug-refractory epilepsy and depression, and more recently has been proposed as a therapeutic treatment of heart conditions such as CHF.

VNS therapy commonly requires implantation of a neurostimulator, a surgical procedure requiring several weeks of recovery before the neurostimulator can be activated and a patient can start receiving VNS therapy. Even after the recovery and activation of the neurostimulator, a full therapeutic dose of VNS is not immediately delivered to the patient to avoid causing significant patient discomfort and other undesirable side effects. Instead, to allow the patient to adjust to the VNS therapy, a titration process is utilized in which the intensity is gradually increased over a period of time under a control of a physician, with the patient given time between successive increases in VNS therapy intensity to adapt to the new intensity. As stimulation is chronically applied at each new intensity level, the patient's tolerance threshold, or tolerance zone boundary, gradually increases, allowing for an increase in intensity during subsequent titration sessions. The titration process can take significantly longer in practice because the increase in intensity is generally performed by a physician or other healthcare provider, and thus, for every step in the titration process to take place, the patient has to visit the provider's office to have the titration adjustments performed. Scheduling conflicts in the provider's office may increase the time between titration sessions, thereby extending the overall titration process, during which the patient in need of VNS does not receive the VNS at the full therapeutic intensity.

For patients receiving VNS therapy for the treatment of epilepsy, a titration process that continues over an extended period of time, such as six to twelve months, may be somewhat acceptable because the patient's health condition typically would not worsen in that period of time. However, for patients being treated for other health conditions, such as CHF, the patient's condition may degrade rapidly if left untreated. As a result, there is a much greater urgency to completing the VNS titration process when treating a patient with a time-sensitive condition, such as CHF.

Accordingly, a need remains for an approach to efficiently titrate neurostimulation therapy for treating chronic cardiac dysfunction and other conditions while minimizing side effects and related discomfort caused by the titration or by the VNS therapy itself.

SUMMARY

Systems and methods are provided for delivering neurostimulation therapies to patients. A titration process is used to gradually increase the stimulation intensity to a desired therapeutic level. This titration process can minimize the amount of time required to complete titration so as to begin delivery of the stimulation at therapeutically desirable levels.

According to one embodiment an implantable vagus nerve stimulation (VNS) system includes a sensor configured to measure ECG data for a patient, a stimulation subsystem configured to deliver VNS to the patient, wherein the VNS is delivered according to a duty cycle comprising an ON period during which a VNS dose is applied and an OFF period during which the VNS dose is suspended, and a control system configured to perform a heart rate variability analysis with the ECG data. Performing the heart rate variability analysis with the ECG data includes measuring R-R intervals between successive R-waves for the ECG data measured during at least a portion of the ON period and at least a portion of the OFF period, wherein the at least a portion of the ON period is a stimulation period and the at least a portion of the OFF period is a baseline period, and plotting each R-R interval against an immediately preceding R-R interval for each of the stimulation period and the baseline period. In some embodiments, performing the heart rate variability analysis further includes determining, based on the plot, at least one of a standard deviation from an axis of a line perpendicular to an identity line for each of the stimulation period plot and the baseline period plot or a centroid of each of the stimulation period plot and the baseline period plot.

According to another embodiment a vagus nerve stimulation (VNS) system includes an external programmer and an implantable system. The implantable system includes a sensor configured to measure ECG data for a patient and transmit the measured ECG to the external programmer and a stimulation subsystem configured to deliver VNS to a patient, wherein the VNS is delivered according to a duty cycle comprising an ON period during which a VNS dose is applied and an OFF period during which the VNS dose is suspended. The external programmer is configured to receive the measured ECG from the implantable system and perform a heart rate variability analysis with the ECG data. The heart rate variability analysis includes measuring R-R intervals between successive R-waves for the ECG data measured during at least a portion of the ON period and at least a portion of the OFF period, wherein the at least a portion of the ON period is a stimulation period and the at least a portion of the OFF period is a baseline period, and plotting each R-R interval against an immediately preceding R-R interval for each of the stimulation period and the baseline period. In some embodiments, the heart rate variability analysis further includes determining, based on the plot, at least one of a standard deviation from an axis of a line perpendicular to an identity line for each of the stimulation period plot and the baseline period plot or a centroid of each of the stimulation period plot and the baseline period plot. In some embodiments, the implantable system further includes a control system configured to control the stimulation subsystem to increase the VNS dose delivered to the patient according to a titration schedule.

According to another embodiment a vagus nerve stimulation (VNS) system includes a local telemetry device and an implantable system. The implantable system includes a sensor configured to measure ECG data for a patient and transmit the measured ECG to the local telemetry device and a stimulation subsystem configured to deliver VNS to the patient, wherein the VNS is delivered according to a duty cycle comprising an ON period during which a VNS dose is applied and an OFF period during which the VNS dose is suspended. The local telemetry device is configured to receive the ECG data from the implantable system and perform a heart rate variability analysis with the ECG data. Performing the heart rate variability analysis includes measuring R-R intervals between successive R-waves for the ECG data measured during at least a portion of the ON period and at least a portion of the OFF period, wherein the at least a portion of the ON period is a stimulation period and the at least a portion of the OFF period is a baseline period, and plotting each R-R interval against an immediately preceding R-R interval for each of the stimulation period and the baseline period. In some embodiments, performing the heart rate variability analysis further includes determining, based on the plot, at least one of a standard deviation from an axis of a line perpendicular to an identity line for each of the stimulation period plot and the baseline period plot or a centroid of each of the stimulation period plot and the baseline period plot. More particularly, in some embodiments, performing the heart rate variability analysis includes determining the centroid of the stimulation period plot and the baseline period plot, and the local telemetry device is further configured to determine a distance between the centroids of the stimulation period plot and the baseline period plot and compare the distance to a threshold value. In some embodiments, the local telemetry device is further configured to, in response to the distance being less than the threshold value, send an alert to a physician of the patient or transmit a command to the implantable system to increase an intensity of the VNS dose applied to the patient. In some embodiments, the implantable system further includes a control system configured to increase the VNS dose delivered to the patient according to a titration schedule. Additionally, in some embodiments, the local telemetry device is configured to perform the heart rate variability analysis in response to an increase in the VNS dose.

According to another embodiment an implantable vagus nerve stimulation (VNS) system includes a sensor configured to measure ECG data for a patient, a stimulation subsystem configured to deliver VNS to the patient, wherein the VNS is delivered according to a duty cycle comprising an ON period during which a VNS dose is applied and an OFF period during which the VNS dose is suspended, and a control system configured to perform a Poincaré analysis with the ECG data. Performing the Poincaré analysis includes measuring R-R intervals between successive R-waves for the ECG data measured during at least a portion of the ON period and at least a portion of the OFF period, wherein the at least a portion of the ON period is a stimulation period and the at least a portion of the OFF period is a baseline period, and plotting each R-R interval against an immediately successive R-R interval for each of the stimulation period and the baseline period. In some embodiments, performing the Poincaré analysis further includes determining, based on the plot, at least one of a standard deviation from an axis of a line perpendicular to an identity line for each of the stimulation period plot and the baseline period plot or a centroid of each of the stimulation period plot and the baseline period plot.

In some embodiments, the control system is further configured to perform the Poincaré analysis by determining, based on the plot, at least one of a standard deviation from an axis of a line perpendicular to an identity line for each of the stimulation period plot and the baseline period plot or a centroid of each of the stimulation period plot and the baseline period plot. More particularly, in some embodiments, performing the Poincaré analysis includes determining the centroid of each of the stimulation period plot and the baseline period plot, and the control system is further configured to determine a distance between the centroids of the stimulation period plot and the baseline period plot and compare the distance to a threshold value. In some embodiments, the control system is further configured to, in response to the distance being less than the threshold value, perform at least one of sending an alert to a physician of the patient or modifying an intensity of the VNS dose applied to the patient. In some embodiments, the control system is further configured to control the stimulation subsystem to increase the VNS dose delivered to the patient according to a titration schedule. Additionally, in some embodiments, the control system is configured to perform the Poincaré analysis in response to an increase in the VNS dose. In some embodiments, the control system is configured to perform the Poincaré analysis periodically. Additionally, in some embodiments, the control system is configured to prepare periodic reports for a physician of the patient based on the Poincaré analysis.

According to another embodiment a vagus nerve stimulation (VNS) system includes an external programmer and an implantable system. The implantable system includes a sensor configured to measure ECG data for a patient and transmit the ECG data to the external programmer and a stimulation subsystem configured to deliver VNS to a patient, wherein the VNS is delivered according to a duty cycle comprising an ON period during which a VNS dose is applied and an OFF period during which the VNS dose is suspended. The external programmer is configured to receive the ECG data from the implantable system and perform a Poincaré analysis with the ECG data. The Poincaré analysis includes measuring R-R intervals between successive R-waves for the ECG data measured during at least a portion of the ON period and at least a portion of the OFF period, wherein the at least a portion of the ON period is a stimulation period and the at least a portion of the OFF period is a baseline period, and plotting each R-R interval against an immediately successive R-R interval for each of the stimulation period and the baseline period. In some embodiments, the Poincaré analysis further includes determining, based on the plot, at least one of a standard deviation from an axis of a line perpendicular to an identity line for each of the stimulation period plot and the baseline period plot or a centroid of each of the stimulation period plot and the baseline period plot.

In some embodiments, the external programmer is further configured to perform the Poincaré analysis by determining, based on the plot, at least one of a standard deviation from an axis of a line perpendicular to an identity line for each of the stimulation period plot and the baseline period plot or a centroid of each of the stimulation period plot and the baseline period plot. More particularly, in some embodiments, performing the Poincaré analysis includes determining the centroid of each of the stimulation period plot and the baseline period plot, and the external programmer is further configured to determine a distance between the centroids of the stimulation period plot and the baseline period plot and compare the distance to a threshold value. In some embodiments, the external programmer is further configured to, in response to the distance being less than the threshold value, display an alert or transmit a command to the implantable system to increase an intensity of the VNS dose applied to the patient. In some embodiments, the implantable system further includes a control system configured to control the stimulation subsystem to increase the VNS dose delivered to the patient according to a titration schedule. In some embodiments, the external programmer is further configured to display the stimulation period plot and the baseline period plot. In some embodiments, the sensor is configured to transmit the ECG data to the external programmer in real-time, and the external programmer is configured to receive the ECG data from the implantable system and perform the Poincaré analysis in real-time.

According to another embodiment a vagus nerve stimulation (VNS) system includes a local telemetry device and an implantable system. The implantable system includes a sensor configured to measure ECG data for a patient and transmit the ECG data to the local telemetry device and a stimulation subsystem configured to deliver VNS to the patient, wherein the VNS is delivered according to a duty cycle comprising an ON period during which a VNS dose is applied and an OFF period during which the VNS dose is suspended. The local telemetry device is configured to receive the ECG data from the implantable system and perform a Poincaré analysis with the ECG data. Performing the Poincaré analysis includes measuring R-R intervals between successive R-waves for the ECG data measured during at least a portion of the ON period and at least a portion of the OFF period, wherein the at least a portion of the ON period is a stimulation period and the at least a portion of the OFF period is a baseline period, and plotting each R-R interval against an immediately preceding R-R interval for each of the stimulation period and the baseline period. In some embodiments, performing the Poincaré analysis further includes determining, based on the plot, at least one of a standard deviation from an axis of a line perpendicular to an identity line for each of the stimulation period plot and the baseline period plot or a centroid of each of the stimulation period plot and the baseline period plot.

In some embodiments, the local telemetry device is further configured to perform the Poincaré analysis by determining, based on the plot, at least one of a standard deviation from an axis of a line perpendicular to an identity line for each of the stimulation period plot and the baseline period plot or a centroid of each of the stimulation period plot and the baseline period plot. More particularly, in some embodiments, performing the Poincaré analysis includes determining the centroid of the stimulation period plot and the baseline period plot, and the local telemetry device is further configured to determine a distance between the centroids of the stimulation period plot and the baseline period plot and compare the distance to a threshold value. In some embodiments, the local telemetry device is further configured to, in response to the distance being less than the threshold value, send an alert to a physician of the patient or transmit a command to the implantable system to increase an intensity of the VNS dose applied to the patient. In some embodiments, the implantable system further includes a control system configured to increase the VNS dose delivered to the patient according to a titration schedule. Additionally, in some embodiments, the local telemetry device is configured to perform the Poincaré analysis in response to an increase in the VNS dose. In some embodiments, the local telemetry device is configured to perform the Poincaré analysis periodically. Additionally, in some embodiments, the local telemetry device is configured to prepare periodic reports for a physician of the patient based on the periodic Poincaré analysis.

DETAILED DESCRIPTION

Various aspects of the disclosure will now be described with regard to certain examples and embodiments, which are intended to illustrate but not to limit the disclosure. Nothing in this disclosure is intended to imply that any particular feature or characteristic of the disclosed embodiments is essential. The scope of protection is defined by the claims that follow this description and not by any particular embodiment described herein. Before turning to the figures, which illustrate example embodiments in detail, it should be understood that the application is not limited to the details or methodology set forth in the description or illustrated in the figures. It should also be understood that the terminology is for the purpose of description only and should not be regarded as limiting.

CHF and other cardiovascular diseases cause derangement of autonomic control of the cardiovascular system, favoring increased sympathetic and decreased parasympathetic central outflow. These changes are accompanied by elevation of basal heart rate arising from chronic sympathetic hyperactivation along the neurocardiac axis.

The vagus nerve is a diverse nerve trunk that contains both sympathetic and parasympathetic fibers, and both afferent and efferent fibers. These fibers have different diameters and myelination, and subsequently have different activation thresholds. This results in a graded response as intensity is increased. Low intensity stimulation results in a progressively greater tachycardia, which then diminishes and is replaced with a progressively greater bradycardia response as intensity is further increased. Peripheral neurostimulation therapies that target the fluctuations of the autonomic nervous system have been shown to improve clinical outcomes in some patients. Specifically, autonomic regulation therapy results in simultaneous creation and propagation of efferent and afferent action potentials within nerve fibers comprising the cervical vagus nerve. The therapy directly improves autonomic balance by engaging both medullary and cardiovascular reflex control components of the autonomic nervous system. Upon stimulation of the cervical vagus nerve, action potentials propagate away from the stimulation site in two directions, efferently toward the heart and afferently toward the brain. Efferent action potentials influence the intrinsic cardiac nervous system and the heart and other organ systems, while afferent action potentials influence central elements of the nervous system.

Figure 1:
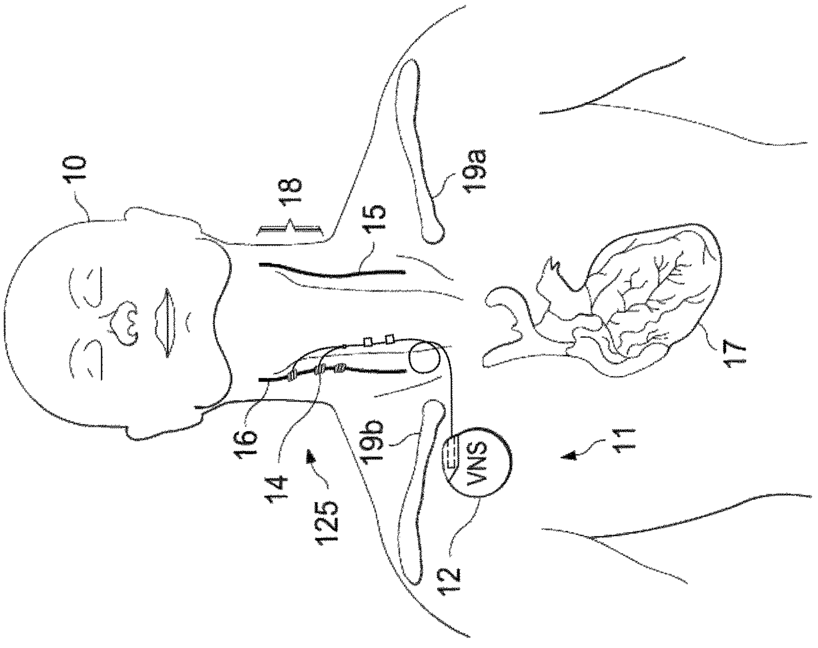
FIG. 1 is a front anatomical diagram showing, by way of example, placement of an implantable vagus stimulation device in a male patient, in accordance with one embodiment.

An implantable vagus nerve stimulator, such as used to treat drug-refractory epilepsy and depression, can be adapted for use in managing chronic cardiac dysfunction (CCD) through therapeutic bi-directional vagus nerve stimulation. FIG. 1 is a front anatomical diagram showing, by way of example, placement of an implantable medical device (e.g., a vagus nerve stimulation (VNS) system 11, as shown in FIG. 1) in a male patient 10, according to an exemplary embodiment. The VNS provided through the stimulation system 11 operates under several mechanisms of action. These mechanisms include increasing parasympathetic outflow and inhibiting sympathetic effects by inhibiting norepinephrine release and adrenergic receptor activation. More importantly, VNS triggers the release of the endogenous neurotransmitter acetylcholine and other peptidergic substances into the synaptic cleft, which has several beneficial anti-arrhythmic, anti-apoptotic, and anti-inflammatory effects as well as beneficial effects at the level of the central nervous system.

The implantable vagus stimulation system 11 comprises an implantable neurostimulator or pulse generator 12 and a stimulating nerve electrode assembly 125. The neurostimulator or pulse generator may be a voltage stimulator or, more preferably, a current stimulator. The stimulating nerve electrode assembly 125, comprising at least an electrode pair, is conductively connected to the distal end of an insulated, electrically conductive lead assembly 13 and electrodes 14. The electrodes 14 may be provided in a variety of forms, such as, e.g., helical electrodes, probe electrodes, cuff electrodes, as well as other types of electrodes.

The implantable vagus stimulation system 11 can be remotely accessed following implant through an external programmer, such as the programmer 40 shown in FIG. 3 and described in further detail below. The programmer 40 can be used by healthcare professionals to check and program the neurostimulator 12 after implantation in the patient 10 and to adjust stimulation parameters during the stimulation titration process. In some embodiments, an external magnet may provide basic controls. For example, an electromagnetic controller may enable the patient 10 or healthcare professional to interact with the implanted neurostimulator 12 to exercise increased control over therapy delivery and suspension. For further example, an external programmer may communicate with the neurostimulation system 11 via other wired or wireless communication methods, such as, e.g., wireless RF transmission. Together, the implantable vagus stimulation system 11 and one or more of the external components form a VNS therapeutic delivery system.

Figure 4:
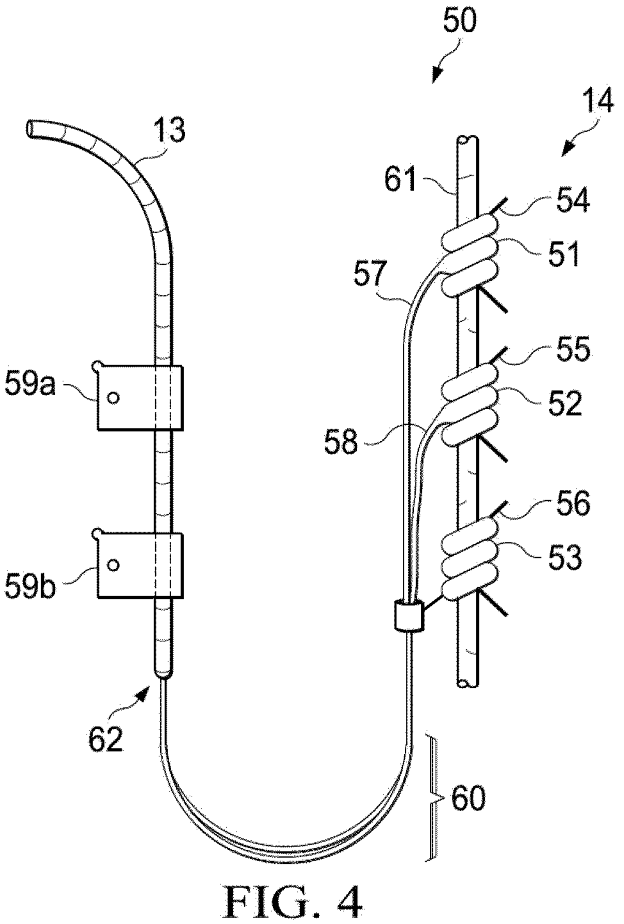
FIG. 4 is a diagram showing electrodes provided as on the stimulation therapy lead of FIG. 2 in place on a vagus nerve in situ, according to an exemplary embodiment.

The neurostimulator 12 is typically implanted in the patient's right or left pectoral region generally on the same side (ipsilateral) as the vagus nerve 15, 16 to be stimulated, although other neurostimulator-vagus nerve configurations, including contra-lateral and bi-lateral are possible. A vagus nerve typically comprises two branches that extend from the brain stem respectively down the left side and right side of the patient, as seen in FIG. 1. The electrodes 14 are generally implanted on the vagus nerve 15, 16 about halfway between the clavicle 19*a-b* and the mastoid process. The electrodes may be implanted on either the left or right side. The lead assembly 13 and electrodes 14 are implanted by first exposing the carotid sheath and chosen branch of the vagus nerve 15, 16 through a latero-cervical incision (perpendicular to the long axis of the spine) on the ipsilateral side of the patient's neck 18. The helical electrodes 14 are then placed onto the exposed nerve sheath and tethered. A subcutaneous tunnel is formed between the respective implantation sites of the neurostimulator 12 and helical electrodes 14, through which the lead assembly 13 is guided to the neurostimulator 12 and securely connected. Additionally, in various embodiments, the neurostimulator 12 connects to the electrodes 14 as shown in FIG. 4 (e.g., at the top helices).

In one embodiment, the neural stimulation is provided as a low level maintenance dose independent of cardiac cycle. The stimulation system 11 bi-directionally stimulates either the left vagus nerve 15 or the right vagus nerve 16. However, it is contemplated that multiple electrodes 14 and multiple leads 13 could be utilized to stimulate simultaneously, alternatively or in other various combinations. Stimulation may be through multimodal application of continuously-cycling, intermittent and periodic electrical stimuli, which are parametrically defined through stored stimulation parameters and timing cycles. Both sympathetic and parasympathetic nerve fibers in the vagosympathetic complex are stimulated. Generally, cervical vagus nerve stimulation results in propagation of action potentials from the site of stimulation in a bi-directional manner. The application of bi-directional propagation in both afferent and efferent directions of action potentials within neuronal fibers comprising the cervical vagus nerve improves cardiac autonomic balance. Afferent action potentials propagate toward the parasympathetic nervous system's origin in the medulla in the nucleus *ambiguus*, nucleus tractus solitarius, and the dorsal motor nucleus, as well as towards the sympathetic nervous system's origin in the intermediolateral cell column of the spinal cord. Efferent action potentials propagate toward the heart 17 to activate the components of the heart's intrinsic nervous system. Either the left or right vagus nerve 15, 16 can be stimulated by the stimulation system 11. The right vagus nerve 16 has a moderately lower (approximately 30%) stimulation threshold than the left vagus nerve 15 for heart rate effects at the same stimulation frequency and pulse width.

Figure 2A:
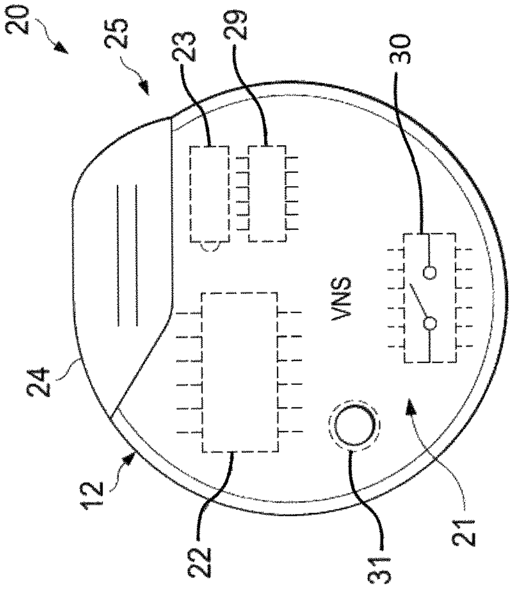
FIGS. 2A and 2B are diagrams respectively showing the implantable neurostimulator and the stimulation therapy lead of FIG. 1, according to an exemplary embodiment.
Figure 2B:
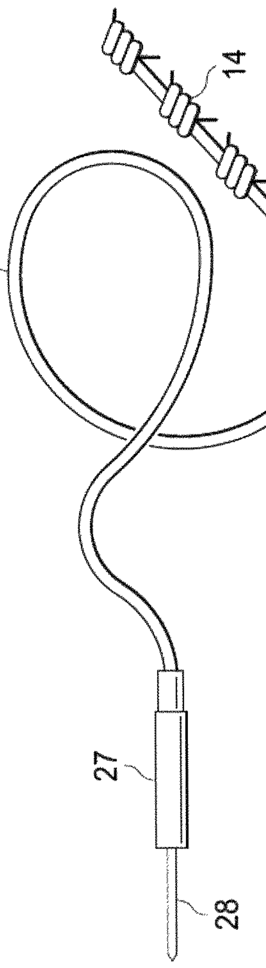

The VNS therapy is delivered autonomously to the patient's vagus nerve 15, 16 through three implanted components that include a neurostimulator 12, lead assembly 13, and electrodes 14. FIGS. 2A and 2B are diagrams respectively showing the implantable neurostimulator 12 and the stimulation lead assembly 13 of FIG. 1. In one embodiment, the neurostimulator 12 can be adapted from a VNS Therapy Demipulse Model 103 or AspireSR Model 106 pulse generator, manufactured and sold by Cyberonics, Inc., Houston, TX, although other manufactures and types of implantable VNS neurostimulators could also be used. The stimulation lead assembly 13 and electrodes 14 are generally fabricated as a combined assembly and can be adapted from a Model 302 lead, PerenniaDURA Model 303 lead, or PerenniaFLEX Model 304 lead, also manufactured and sold by Cyberonics, Inc., in three sizes based, for example, on a helical electrode inner diameter, although other manufactures and types of single-pin receptacle-compatible therapy leads and electrodes could also be used.

Referring first to FIG. 2A, the system 20 may be configured to provide multimodal vagus nerve stimulation. In a maintenance mode, the neurostimulator 12 is parametrically programmed to deliver continuously-cycling, intermittent and periodic ON-OFF cycles of VNS. Such delivery produces action potentials in the underlying nerves that propagate bi-directionally, both afferently and efferently.

The neurostimulator 12 includes an electrical pulse generator that is tuned to improve autonomic regulatory function by triggering action potentials that propagate both afferently and efferently within the vagus nerve 15, 16. The neurostimulator 12 is enclosed in a hermetically scaled housing 21 constructed of a biocompatible material, such as titanium. The housing 21 contains electronic circuitry 22 powered by a battery 23, such as a lithium carbon monofluoride primary battery or a rechargeable secondary cell battery. The electronic circuitry 22 may be implemented using complementary metal oxide semiconductor integrated circuits that include a microprocessor controller that executes a control program according to stored stimulation parameters and timing cycles; a voltage regulator that regulates system power; logic and control circuitry, including a recordable memory 29 within which the stimulation parameters are stored, that controls overall pulse generator function, receives and implements programming commands from the external programmer, or other external source, collects and stores telemetry information, processes sensory input, and controls scheduled and sensory-based therapy outputs; a transceiver that remotely communicates with the external programmer using radio frequency signals; an antenna, which receives programming instructions and transmits the telemetry information to the external programmer; and a reed switch 30 that provides remote access to the operation of the neurostimulator 12 using an external programmer, a simple patient magnet, or an electromagnetic controller. The recordable memory 29 can include both volatile (dynamic) and non-volatile/persistent (static) forms of memory, within which the stimulation parameters and timing cycles can be stored. Other electronic circuitry and components are possible.

The neurostimulator 12 includes a header 24 to securely receive and connect to the lead assembly 13. In one embodiment, the header 24 encloses a receptacle 25 into which a single pin for the lead assembly 13 can be received, although two or more receptacles could also be provided, along with the corresponding electronic circuitry 22. The header 24 may internally include a lead connector block (not shown), a setscrew, and a spring contact (not shown) that electrically connects to the lead ring, thus completing an electrical circuit.

In some embodiments, the housing 21 may also contain a heart rate sensor 31 that is electrically interfaced with the logic and control circuitry, which receives the patient's sensed heart rate as sensory inputs. The heart rate sensor 31 monitors heart rate using an ECG-type electrode. Through the electrode, the patient's heart beat can be sensed by detecting ventricular depolarization. In a further embodiment, a plurality of electrodes can be used to sense voltage differentials between electrode pairs, which can undergo signal processing for cardiac physiological measures, for instance, detection of the P-wave, QRS complex, and T-wave. The heart rate sensor 31 provides the sensed heart rate to the control and logic circuitry as sensory inputs that can be used to determine the onset or presence of arrhythmias, particularly VT, and/or to monitor and record changes in the patient's heart rate over time or in response to applied stimulation signals.

Referring next to FIG. 2B, the lead assembly 13 delivers an electrical signal from the neurostimulator 12 to the vagus nerve 15, 16 via the electrodes 14. On a proximal end, the lead assembly 13 has a lead connector 27 that transitions an insulated electrical lead body to a metal connector pin 28 with a metal connector ring. During implantation, the connector pin 28 is guided through the receptacle 25 into the header 24 and securely fastened in place using the setscrew (not shown) to electrically couple one electrode of the lead assembly 13 to the neurostimulator 12 while a spring contact (not shown) makes electrical contact to the ring connected to the other electrode. On a distal end, the lead assembly 13 terminates with the electrode 14, which bifurcates into a pair of anodic and cathodic electrodes 62 (as further described infra with reference to FIG. 4). In one embodiment, the lead connector 27 is manufactured using silicone and the connector pin 28 and ring are made of stainless steel, although other suitable materials could be used, as well. The insulated lead body 13 utilizes a silicone-insulated alloy conductor material.

In some embodiments, the electrodes 14 are helical and placed around the cervical vagus nerve 15, 16 at the location below where the superior and inferior cardiac branches separate from the cervical vagus nerve. In alternative embodiments, the helical electrodes may be placed at a location above where one or both of the superior and inferior cardiac branches separate from the cervical vagus nerve. In one embodiment, the helical electrodes 14 are positioned around the patient's vagus nerve oriented with the end of the helical electrodes 14 facing the patient's head. In an alternate embodiment, the helical electrodes 14 are positioned around the patient's vagus nerve 15, 16 oriented with the end of the helical electrodes 14 facing the patient's heart 17. At the distal end, the insulated electrical lead body 13 is bifurcated into a pair of lead bodies that are connected to a pair of electrodes. The polarity of the electrodes could be configured into a proximal anode and a distal cathode, or a proximal cathode and a distal anode.

The neurostimulator 12 may be interrogated prior to implantation and throughout the therapeutic period with a healthcare provider-operable control system comprising an external programmer and programming wand (shown in FIG. 3) for checking proper operation, downloading recorded data, diagnosing problems, and programming operational parameters. FIG. 3 is a diagram showing an external programmer 40 for use with the implantable neurostimulator 12 of FIG. 1. The external programmer 40 includes a healthcare provider operable programming computer 41 and a programming wand 42. Generally, use of the external programmer is restricted to healthcare providers, while more limited manual control is provided to the patient through "magnet mode."

In one embodiment, the external programmer 40 executes application software 45 specifically designed to interrogate the neurostimulator 12. The programming computer 41 interfaces to the programming wand 42 through a wired or wireless data connection. The programming wand 42 can be adapted from a Model 201 Programming Wand, manufactured and sold by Cyberonics, Inc., and the application software 45 can be adapted from the Model 250 Programming Software suite, licensed by Cyberonics, Inc. Other configurations and combinations of external programmer 40, programming wand 42 and application software 45 are possible.

The programming computer 41 can be implemented using a general purpose programmable computer and can be a personal computer, laptop computer, ultrabook computer, netbook computer, handheld computer, tablet computer, smart phone, or other form of computational device. For example, in one embodiment, the programming computer 41 is a tablet programmer with a wired or wireless data connection to the programming wand 42. The programming computer 41 functions through those components conventionally found in such devices, including, for instance, a central processing unit, volatile and persistent memory, touch-sensitive display, control buttons, peripheral input and output ports, and network interface. The computer 41 operates under the control of the application software 45, which is executed as program code as a series of process or method modules or steps by the programmed computer hardware. Other assemblages or configurations of computer hardware, firmware, and software are possible.

Operationally, the programming computer 41, when connected to a neurostimulator 12 through wireless telemetry using the programming wand 42, can be used by a healthcare provider to remotely interrogate the neurostimulator 12 and modify stored stimulation parameters. The programming wand 42 provides data conversion between the digital data accepted by and output from the programming computer and the radio frequency signal format that is required for communication with the neurostimulator 12. In other embodiments, the programming computer may communicate with the implanted neurostimulator 12 using other wireless communication methods, such as wireless RF transmission. The programming computer 41 may further be configured to receive inputs, such as physiological signals received from patient sensors (e.g., implanted or external). These sensors may be configured to monitor one or more physiological signals, e.g., vital signs, such as body temperature, pulse rate, respiration rate, blood pressure, etc. These sensors may be coupled directly to the programming computer 41 or may be coupled to another instrument or computing device which receives the sensor input and transmits the input to the programming computer 41. The programming computer 41 may monitor, record, and/or respond to the physiological signals in order to effectuate stimulation delivery in accordance with some embodiments.

The healthcare provider operates the programming computer 41 through a user interface that includes a set of input controls 43 and a visual display 44, which could be touch-sensitive, upon which to monitor progress, view downloaded telemetry and recorded physiology, and review and modify programmable stimulation parameters. The telemetry can include reports on device history that provide patient identifier, implant date, model number, serial number, magnet activations, total ON time, total operating time, manufacturing date, and device settings and stimulation statistics and on device diagnostics that include patient identifier, model identifier, serial number, firmware build number, implant date, communication status, output current status, measured current delivered, lead impedance, and battery status. Other kinds of telemetry or telemetry reports are possible.

During interrogation, the programming wand 42 is held by its handle 46 and the bottom surface 47 of the programming wand 42 is placed on the patient's chest over the location of the implanted neurostimulator 12. A set of indicator lights 49 can assist with proper positioning of the wand and a set of input controls 48 enable the programming wand 42 to be operated directly, rather than requiring the healthcare provider to awkwardly coordinate physical wand manipulation with control inputs via the programming computer 41. The sending of programming instructions and receipt of telemetry information occur wirelessly through radio frequency signal interfacing. Other programming computer and programming wand operations are possible.

FIG. 4 is a diagram showing the helical electrodes 14 provided as on the stimulation lead assembly 13 of FIG. 2 in place on a vagus nerve 15, 16 in situ 50. Although described with reference to a specific manner and orientation of implantation, the specific surgical approach and implantation site selection particulars may vary, depending upon physician discretion and patient physical structure.

Under one embodiment, helical electrodes 14 may be positioned on the patient's vagus nerve 61 oriented with the end of the helical electrodes 14 facing the patient's head. At the distal end, the insulated electrical lead body 13 is bifurcated into a pair of lead bodies 57, 58 that are connected to a pair of electrodes 51, 52. The polarity of the electrodes 51, 52 could be configured into a proximal anode and a distal cathode, or a proximal cathode and a distal anode. In addition, an anchor tether 53 is fastened over or in connection with the lead bodies 57, 58 that maintains the helical electrodes' position on the vagus nerve 61 following implant. In one embodiment, the conductors of the electrodes 51, 52 are manufactured using a platinum and iridium alloy, while the helical materials of the electrodes 51, 52 and the anchor tether 53 are a silicone elastomer.

During surgery, the electrodes 51, 52 and the anchor tether 53 are coiled around the vagus nerve 61 proximal to the patient's head, each with the assistance of a pair of sutures 54, 55, 56, made of polyester or other suitable material, which help the surgeon to spread apart the respective helices. The lead bodies 57, 58 of the electrodes 51, 52 are oriented distal to the patient's head and aligned parallel to each other and to the vagus nerve 61. A strain relief bend 60 can be formed on the distal end with the insulated electrical lead body 13 aligned, for example, parallel to the helical electrodes 14 and attached to the adjacent fascia by a plurality of tie-downs 59*a-b*.

The neurostimulator 12 delivers VNS under control of the electronic circuitry 22. The stored stimulation parameters are programmable. Each stimulation parameter can be independently programmed to define the characteristics of the cycles of therapeutic stimulation and inhibition to ensure optimal stimulation for a patient 10. The programmable stimulation parameters include output current, signal frequency, pulse width, signal ON time, signal OFF time, magnet activation (for VNS specifically triggered by "magnet mode"), and reset parameters. Other programmable parameters are possible. In addition, sets or "profiles" of preselected stimulation parameters can be provided to physicians with the external programmer and fine-tuned to a patient's physiological requirements prior to being programmed into the neurostimulator 12.

Therapeutically, the VNS may be delivered as a multimodal set of therapeutic doses, which are system output behaviors that are pre-specified within the neurostimulator 12 through the stored stimulation parameters and timing cycles implemented in firmware and executed by the microprocessor controller. The therapeutic doses include a maintenance dose that includes continuously-cycling, intermittent and periodic cycles of electrical stimulation during periods in which the pulse amplitude is greater than 0 mA ("therapy ON") and during periods in which the pulse amplitude is 0 mA ("therapy OFF").

The neurostimulator 12 can operate either with or without an integrated heart rate sensor. Additionally, where an integrated leadless heart rate monitor is available, the neurostimulator 12 can provide autonomic cardiovascular drive evaluation and self-controlled titration. Finally, the neurostimulator 12 can be used to counter natural circadian sympathetic surge upon awakening and manage the risk of cardiac arrhythmias during or attendant to sleep, particularly sleep apneic episodes.

Several classes of implantable medical devices provide therapy using electrical current as a stimulation vehicle. When such a system stimulates certain organs or body structures like the vagus nerve, therapeutic levels of electrical stimulation are usually not well tolerated by patients without undergoing a process known as titration. Titration is a systematic method or process of incrementally increasing the stimulation parameters employed by an implanted device to deliver a stimulation current to the patient at increasing levels that achieve or improve therapeutic benefit while minimizing side effects that could disrupt the stimulation therapy. Titration usually involves bringing the patient to an initial stimulation level that is tolerable to the patient (i.e., below an initial tolerance threshold), waiting for a period of time for the patient to adjust to the continuing delivery of the initial stimulation level and to define a higher tolerance threshold of the patient, and then increasing the initial stimulation level to a higher stimulation level that is, in some patients, greater than the initial tolerance threshold, and so on. This process is repeated in sequences that progress from a stimulation delivery provided over a waiting period, and then to an increase in a stimulation level than defines the next sequence of the stimulation delivery and the next waiting period.

Figure 5:
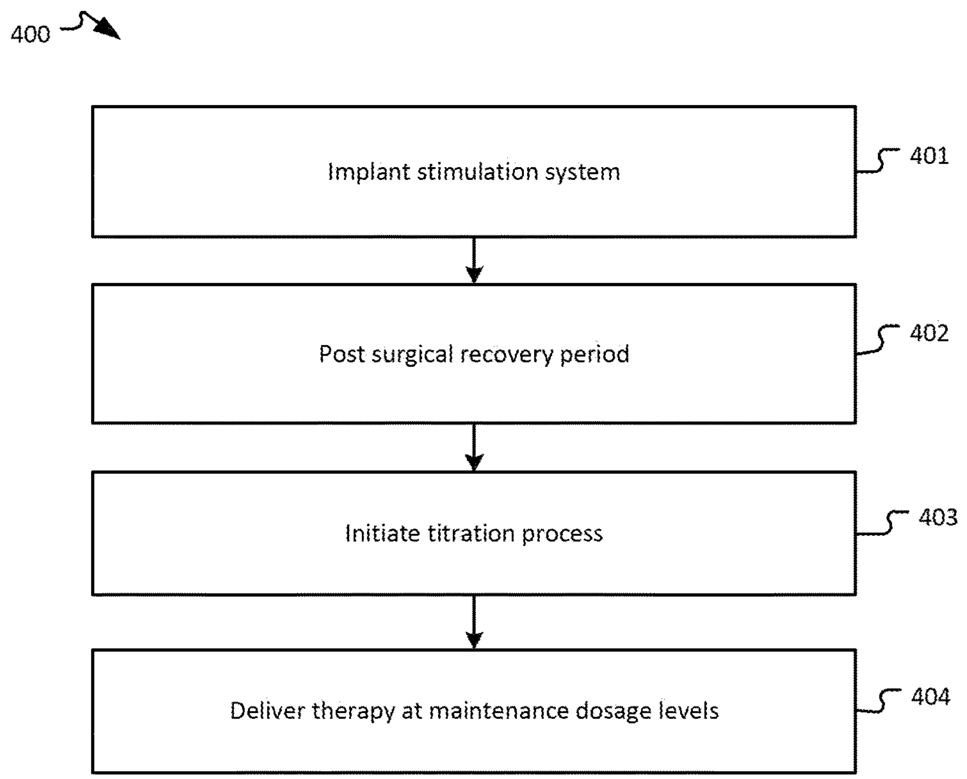
FIG. 5 is a flowchart of a method for delivering vagus nerve stimulation therapy, according to an exemplary embodiment.

FIG. 5 is a flow diagram showing a method for delivering vagus nerve stimulation therapy, according to an exemplary embodiment. A titration process 400 is used to gradually increase the stimulation intensity to a desired therapeutic level or maintenance dosage level. If the stimulation intensity is increased too quickly before the patient is fully accommodated to the stimulation signal, the patient may experience undesirable side effects, such as coughing, hoarseness, throat irritation, or expiratory reflex. The titration process gradually increases stimulation intensity within a tolerable level, and maintains that intensity for a period of time to permit the patient to adjust to each increase in intensity, thereby gradually increasing the patient's side effect tolerance zone boundary to so as to accommodate subsequent increases in intensity. The titration process continues until adequate adaptation is achieved. In embodiments, the titration process is automated and is executed by the implanted device without manual adjustment of the stimulation intensity by the subject or health care provider. As will be described in greater detail below, adequate adaptation is a composite threshold comprising one or more of the following: an acceptable side effect level, a target intensity level, and a target physiological response. In some embodiments, adequate adaption includes all three objectives: an acceptable side effect level, a target intensity level, and a target physiological response.

In some embodiments, the titration process is a mix of automation and physician input. As will be described in greater detail below, a physician may use intermediate holds to stop the automated titration at certain thresholds (e.g., a certain number of days or weeks, certain stimulation parameter values, etc.) and evaluate the patient before resuming the automated titration. The physician may receive a graphical titration history to review how the automated titration process has been progressing from one sequence to the next. The graphical titration history may include markers. The markers may represent intermediate holds, when target parameters are reached between adjacent sequences, etc. After the physician has resumed the automatic titration, the next sequence of automated titration may progress until the next intermediate hold is reached.

As described above, it may be desirable to minimize the amount of time required to complete the titration process so as to begin delivery of the stimulation at therapeutically desirable levels, particularly when the patient is being treated for an urgent condition such as CHF. In addition, it is desirable to utilize a maintenance dose intensity at the minimum level required to achieve the desired therapeutic effect. This can reduce power requirements for the neurostimulator and reduce patient discomfort.

It has been observed that a patient's side effect profile is more sensitive to the stimulation output current than to the other stimulation parameters, such as frequency, pulse width, and duty cycle. As a result, accommodation to the stimulation output current is a primary factor in completing the titration process. It has also been observed that if the other stimulation parameters are maintained at a level below the target levels, the output current can be increased to higher levels without eliciting undesirable side effects that would be result when the other parameters are at the target level. As a result, increasing the target output current while maintaining the other stimulation parameters (pulse width in particular) at reduced levels can result in a faster accommodation and shorter overall titration time than would be achieved by attempting to increase the output current while stimulating at the target pulse width.

Referring again to FIG. 5, in step 401, a stimulation system 11, including a neurostimulator 12, a nerve stimulation lead assembly 13, and a pair of electrodes 14, is implanted in the patient. In step 402, the patient undergoes an optional post-surgery recovery period, during which time the surgical incisions are allowed to heal and no VNS therapy occurs. This period may last, e.g., two weeks post surgery. In step 403, the stimulation therapy is initiated with the initiation of a titration process. During this titration process, VNS therapy is titrated by adjusting one or more of the stimulation parameters, including output current, pulse width, signal frequency, and duty cycle, as will be described in greater detail below. Completion of the titration process determines the stimulation intensity to be used for subsequent maintenance doses delivered in step 404. These maintenance doses may be selected to provide the minimum stimulation intensity necessary to provide the desired therapeutic result.

Figure 6A:
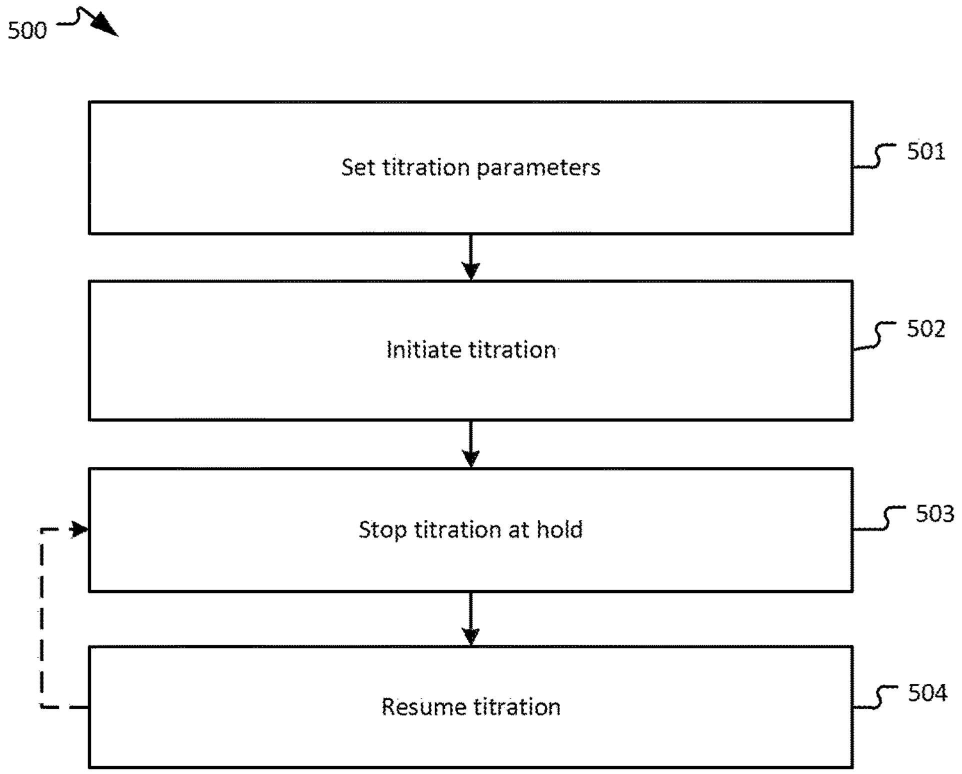
FIGS. 6A and 6B are flowcharts of a titration process, according to an exemplary embodiment.

FIG. 6A is a flow diagram illustrating a titration process 500, according to an exemplary embodiment. Process 500 includes setting titration parameters (step 501), initiating titration (step 502), stopping titration at an intermediate hold (step 503) and resuming titration (step 504).

In step 501, a physician sets the titration parameters via programmer 40, which are received by the implantable vagus nerve stimulation system 11. In some embodiments, the titration parameters may be defined by one or more titration algorithms that may be selected by the physician, or may be presented to the physician as a preferred or recommended list of titration parameters that the programming physician can adopt. In other embodiments, rather than present the physician with a set titration algorithm with fixed algorithm values, the physician may be presented with default values that could be manually adjusted. The titration parameter starting values, target values, and/or increment values for amplitude, pulse width, frequency, and/or duty cycle may be adjustable, as may the time interval between titration steps. Time of day and delay to therapy start may also be programmable as a titration parameter. The titration parameters may also include one or more intermediate holds that maintain certain parameters until the physician indicates that the automated titration can continue. The physician may be limited so that modification can be made to only a select group of parameters, or some parameters may be considered to be in a locked state until unlocked by the physician. In some embodiments, the physician is able to modify a large number of titration parameters (e.g., 10-12 parameters). Alternatively, rather than give the physician control over the titration parameter values themselves, the physician's options for the titration process may be presented as a set of "aggressiveness" options to select from, each of which would be used by the system to determine the values to use. For example, the physician may be able to choose from an aggressive profile, a moderate profile, or a light profile (sensitive) that is appropriate for certain types of patients that do not require detailed titration parameter programming. More or fewer aggressiveness profiles could be used, and the aggressiveness profiles may correspond to the overall health status of the patient, the patient's sensitivity to stimulation therapies or titration processes, or the patient's medical history. The aggressiveness profile selected by the physician may result in a predetermined set of titration parameters being selected. The predetermined titration parameters may vary between different aggressiveness profiles, and some titration parameters may remain constant, or similar, between various aggressiveness profiles. For example, the aggressive profile may be suitable for patients that have a high toleration for the titration process and may include shorter time intervals between titration steps, higher intensity target values, and/or larger increment values (e.g., as compared to the moderate or light profiles) that may result in an achievement of a suitable therapy level more quickly as compared to the moderate or light profiles. While some of the parameters may promote a more aggressive titration progression, some of the parameters may be consistent with parameters of other profiles (e.g., titration holds). In some embodiments, each of the aggressiveness profiles may be mapped by the system to a set of parameters or a range of parameters. For example, if the user selects the aggressive profile, the system may receive the user selection and set the values of one or more parameters (e.g., amplitude, pulse width, frequency, duty cycle, intervals between titration steps, and/or other parameters) to a first set of values. If the user selects the moderate profile, the system may set the values of the parameters to a second predetermined set or range of values that is different than the set associated with the aggressive profile. In some embodiments, the physicians are limited to modification of the parameters within a range of boundary values. The ranges may be for the default parameters, or may be set individually for the aggressiveness options (e.g., the ranges for the aggressive profile and the moderate profile may be different, but may overlap for some parameters). The physician may be able to customize the parameters in the preset profiles. In step 502, the physician initiates titration using the titration parameters defined at 501.

In step 503, titration is stopped at a titration hold. The titration hold may be an intermediate hold set by the physician during step 501. The VNS system 11 may perform automated titration according to process 600, described below. However, the physician is given the option (through the programmer 40) to designate intermediate points at which the titration algorithm would pause and await manual (programmer-based) activation by the physician. These hold points may be either time based (e.g. after 2, 4, 6, and/or 8 weeks of titration) or stimulation based (e.g. once stimulation amplitude reaches 1.0, 1.5, 2.0, and/or 2.5 mA). This would allow the physician to evaluate the patient in the clinic before deciding to continue titration. The physician releases the hold on the titration with the programmer 40 once the patient has been evaluated. The physician may also modify parameters during the clinical evaluations.

The holds may be predefined for the entire titration process during initial set up. Alternatively, the physician may have the option of setting a new intermediate hold when evaluating the patient. The intermediate holds may be consistent throughout the titration process (e.g., every 2 weeks, every 0.5 mA, etc.). In another embodiment, the intermediate holds are different for at least one hold (e.g., 4 weeks to the first hold, 2 weeks for every subsequent hold, etc.). In another embodiment, intermediate holds can be a combination of parameters (e.g., amplitude and pulse width). In some embodiments, the hold may be set to begin when both parameters are met, or when one parameter is met. In another embodiment, one parameter cannot exceed the hold value and will remain constant until the second parameter is reached. In some embodiments, both parameters will progress according to the automated titration until both parameters meet the intermediate hold value, but one parameter may exceed the intermediate hold until the second parameter reaches the intermediate hold value. The physician may have the option to set as many or as few intermediate holds as desired.

During the automated titration between intermediate holds, the VNS system 11 may be fully automated or partially automated. In some embodiments, titration is performed without any intervention from either the patient or the healthcare provider. This embodiment also automatically detects patient side effects and intolerance, and adjusts stimulation parameters to remain below the side effect threshold, as is described with respect to FIG. 6B. In another embodiment, the VNS system 11 may automatically adjust stimulation parameters slowly over time, without any additional intervention from the healthcare provider. Because the system may not be able to determine if stimulation causes an intolerable side effect, it may be configured to rely on the patient to swipe a magnet to indicate an intolerable level of a side effect. The VNS system 11 may then adjust stimulation parameters in response to patient magnet activation.

For example, patients may require a total of 10±2 clinic visits over a 10-week period to reach the target stimulation intensity. The frequency of required clinic visits is bothersome to both patients and providers, and creates a barrier to therapy adoption. In addition, the frequency of required clinic visits extends the time required to titrate patients to the target stimulation intensity. However, physician may be skeptical of completely automated titration and want to ensure the patients are not experiencing intolerable side effects and are adapting to stimulation adequately. By allowing the physician to set the parameters, and evaluate the patient intermediately, but still allow titration to perform automatically between visits, the time period to reach the target stimulation may be reduced, while giving the physicians more control over the titration process. Preferably, the number of clinic visits needed and the overall timeframe of the titration process is reduced by only the use of intermediate holds. Any time penalty related to the intermediate holds is believed to be significantly less than the time penalty resulting from an automated titration process that causes side effect and ultimately requires the patient to undergo a re-titration protocol.

In step 504, titration is resumed. The physician may resume titration using the programmer 40 after evaluation of the patient. When the physician resumes titration, they may have the option to modify stimulation parameters and/or intermediate holds. The titration may resume using automated titration until the next intermediate hold is reached. This process may continue until the therapy parameters are reached.

Figure 6B:
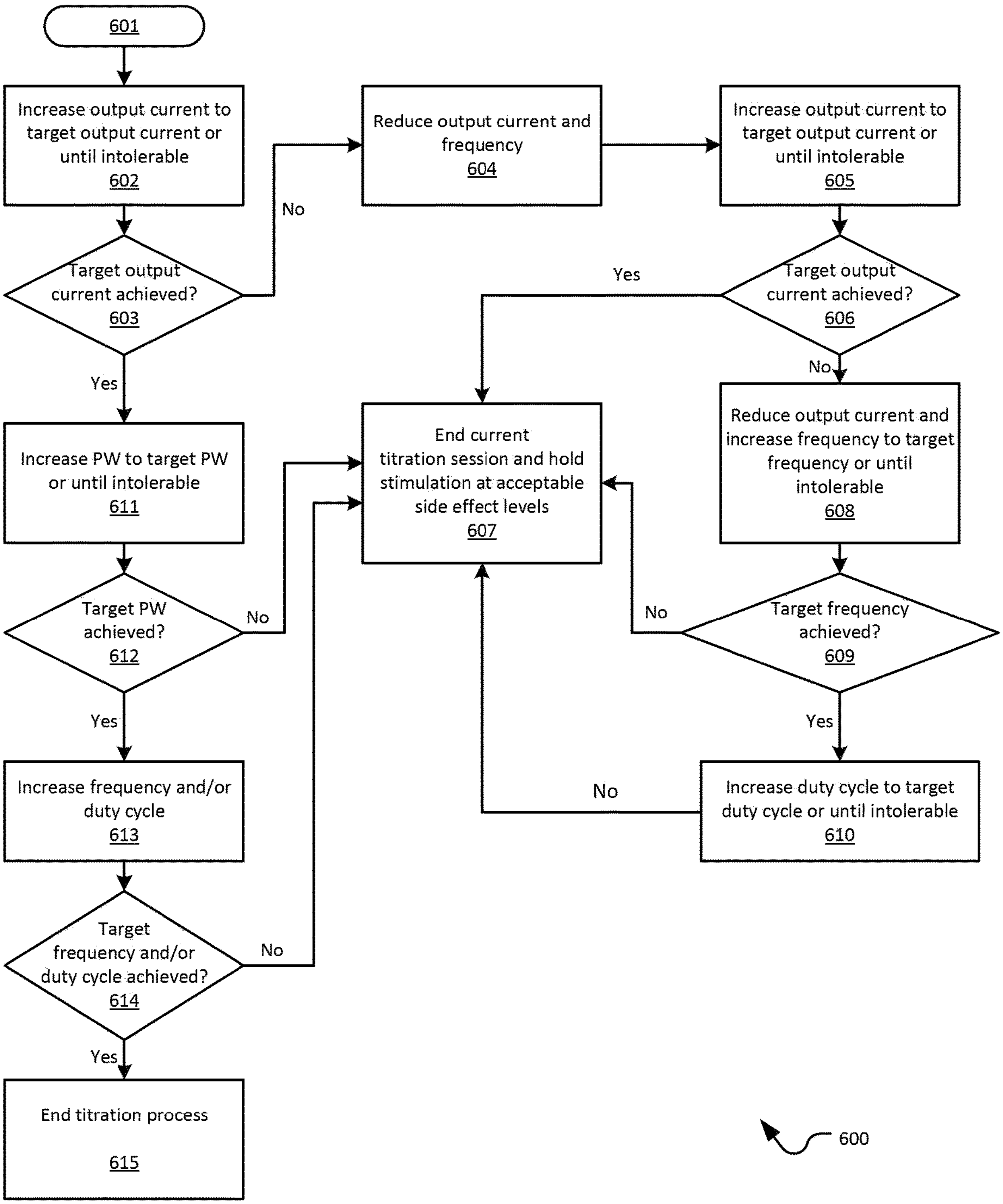

FIG. 6B is a flow diagram illustrating a titration process 600 in accordance with exemplary embodiments. When first initiating the titration process, the neurostimulator 12 is configured to generate a stimulation signal having an initial stimulation parameter set. The initial parameter set may comprise an initial output current, an initial frequency, an initial pulse width, and an initial duty cycle. The various initial parameter settings may vary, but may be selected so that one or more of the parameters are set at levels below a predefined target parameter set level, such that the titration process is used to gradually increase the intensity parameters to achieve adequate adaptation. In some embodiments, the initial frequency is set at the target frequency level, while the initial output current, initial pulse width, and initial duty cycle are set below their respective target levels. In one embodiment, the target parameter set comprises a 10 Hz frequency, 250 μsec pulse width, a duty cycle of 14 sec ON and 1.1 minutes OFF, and an output current of between 1.5 mA-3.0 mA (e.g., 2.5 mA for right side stimulation and 3.0 mA for left side stimulation), and the initial parameter set comprises 10 Hz frequency, 130 μsec pulse width, a duty cycle of 14 sec ON and 1.1 minutes OFF, and an output current of between 0.25 mA-0.5 mA. In other embodiments, the target parameter set includes a 5 Hz frequency that is used instead of a 10 Hz frequency. The initial parameter set may also include one or more intermediate holds as discussed with respect to FIG. 6A. However, this is an exemplary embodiment and these values are not intended to be limiting. Other frequencies, pulse widths, duty cycles and output currents may be implemented. The initial and target parameters may vary from patient to patient based on the patient's sensitivity to stimulation. While the initial parameters are shown to be equal to the target parameters for some of the exemplary parameters (e.g., frequency and duty cycle), some or all of the parameters may have initial parameters that differ from the target parameters.

In step 601, the stimulation system delivers stimulation to the patient. If this is the first titration session, then the stimulation would be delivered with the initial stimulation parameter set described above. If this is a subsequent titration session, then the stimulation intensity would remain at the same level provided at the conclusion of the previous titration session. Alternatively, the subsequent titration session can start at a level that is set by the physician, e.g., at the next titration level that follows the level provided at the conclusion of the previous titration session.

In step 602, the output current is gradually increased until the stimulation results in an intolerable side effect level, the target intensity (e.g., 2.5 mA at a pulse width of 250 us and frequency of 10 Hz) is reached, or adequate adaptation is achieved. As described above, adequate adaptation is a composite threshold comprising one or more of the following: an acceptable side effect level, a target intensity level, and a target physiological response. In accordance with some embodiments, the target physiological response comprises a target heart rate change during stimulation. The patient's heart rate may be monitored using an implanted or external heart rate monitor, and the patient's heart rate during stimulation is compared to the patient's baseline heart rate to determine the extent of heart rate change. In accordance with some embodiments, the target heart rate change is a heart rate change of between 4% and 5%. If at any point during the titration process 600 adequate adaptation is achieved, the titration process ends and the stimulation intensity which resulted in the adequate adaptation is used for ongoing maintenance dose therapy delivery.

The output current may be increased in any desired increment, but small increments, e.g., 0.1 mA or 0.25 mA, may be desirable so as to enable more precise adjustments. In some cases, the output current increments may be determined by the neurostimulator's maximum control capability. During the initial titration sessions, it is likely that the patient's side effect tolerance zone boundary will be reached well before the output current reaches the target level or adequate adaptation is achieved. At decision step 603, if the target output current has not been achieved but the maximum tolerable side effects have been exceeded, the process proceeds to step 604.

In step 604, the output current is reduced one increment to bring the side effects within acceptable levels. In addition, the frequency is reduced. In embodiments in which the initial frequency was 10 Hz, in step 604, the frequency may be reduced, e.g., to 5 Hz or 2 Hz.

Next, in step 605, the output current is gradually increased again at the reduced frequency level until the stimulation results in an intolerable side effect level or the target output current (e.g., 2.5 mA) is reached. At decision step 606, if the target output current has been reached and the maximum tolerable side effects have not been exceeded, the process proceeds to step 607 where the titration session is concluded. The stimulation system may be programmed to continue delivering the stimulation signal at the last parameter settings achieved prior to conclusion of the titration session. After a period of time, another titration session may be initiated and the process returns to step 601. This can be any period of time sufficient to permit the patient to adjust to the increased stimulation levels. This can be, for example, as little as approximately two or three days, approximately one to two weeks, approximately four to eight weeks, or any other desired period of time.

In some embodiments, the titration sessions are automatically initiated by the stimulation system or initiated by the patient without requiring any intervention by the health care provider. This can eliminate the need for the patient to schedule a subsequent visit to the health care provider, thereby potentially reducing the total amount of time needed for the titration process to complete. In these embodiments, the stimulation system may include a physiological monitor, e.g., an implanted heart rate sensor, that communicates with the stimulation system's control system to enable the control system to detect the patient's physiological response to the titration and automatically make adjustments to the titration processes described herein with reduced or no inputs from the patient or health care provider. The monitored signals can also enable the control system to detect when the target physiological response has been achieved and conclude the titration process. The stimulation system could in addition or alternatively include a patient control input to permit the patient to communicate to the control system that the acceptable side effect level has been exceeded. This control input may comprise an external control magnet that the patient can swipe over the implanted neurostimulator, or other internal or external communication device that the patient can use to provide an input to the control system. In these automatically initiated titration sessions, the stimulation system may be configured to wait a period of time after completing one session before initiating the next session. This period of time may be predetermined, e.g., two or three days, or programmable. In another embodiment, the stimulation system is configured to wait until authorization has been received before initiating the next session (i.e., an intermediate hold).

Returning to decision step 606, if the target output current has not been reached but the maximum tolerable side effects have been exceeded, the process proceeds to step 608. In step 608, the output current is reduced one increment to restore an acceptable side effect condition, and the frequency is gradually increased until the stimulation results in an intolerable side effect level or the target frequency (e.g., 10 Hz) is reached. At decision step 609, if the target frequency has not been reached but the maximum tolerable side effects have been exceeded, the frequency is reduced to restore an acceptable side effect level and the process proceeds to step 607. Again, in step 607, the current titration session is concluded and the stimulation system may be programmed to continue delivering the stimulation signal at the last parameter settings achieved prior to conclusion of the titration session.

At decision step 609, if the target frequency has been reached before the maximum tolerable side effects have been exceeded, the duty cycle is gradually increased until the stimulation results in an intolerable side effect level or the target duty cycle (e.g., 14 sec ON and 1.1 min OFF) is reached, at which point the process proceeds to step 607 and the titration session is concluded and ongoing stimulation delivered at the last intensity eliciting acceptable side effect levels.

Returning to decision step 603, if the target output current has been achieved before the maximum tolerable side effects are exceeded, the process proceeds to step 611. In step 611, the pulse width is gradually increased until the stimulation results in an intolerable side effect level or the target pulse width (e.g., 250 μsec) is reached. In some embodiments, before step 611, the output current is reduced (e.g., by up to 50%), and the pulse width may be increased in step 611 at that reduced output current. After the target pulse width is achieved, the output current may be restored to the target output current. In other embodiments, the output current may be reduced (or may be retained at the reduced level established prior to step 611, as described above), and the frequency and duty cycle are gradually increased in step 613 at that reduced output current. This reduction in output current after achieving the target output current may enable the patient to maintain tolerability with increasing pulse width, frequency, and duty cycle in subsequent titration steps.

At decision step 612, if the target pulse width has not been achieved before the maximum tolerable side effects have been exceeded, the pulse width is reduced to restore an acceptable side effect level and the process proceeds to step 607. Again, in step 607, the current titration session is concluded.

If at decision step 612, the target pulse width has been achieved before the maximum tolerable side effects have been exceeded, the process proceeds to step 613. In step 613, the frequency and/or duty cycle are increased until the stimulation results in an intolerable side effect level or the target frequency and target duty cycle are reached. The frequency and duty cycle can be increased in step 612 simultaneously, sequentially, or on an alternating basis.

At decision step 614, if the target frequency and/or target duty cycle have not been achieved before the maximum tolerable side effects have been exceeded, the pulse width and/or frequency are reduced to restore an acceptable side effect level and the process continues to step 607 and the titration session is concluded. In some embodiments, the conclusion of the titration session represented in step 607 indicates an intermediate hold has been reached. A new titration session could then be initiated after visiting a physician to release the intermediate hold.

At decision step 614, if the target pulse width and target frequency have been achieved before the maximum tolerable side effects have been exceeded, all of the stimulation parameters will have reached their target levels and the titration process concludes at step 615. The stimulation therapy may proceed with the maintenance dose at the target stimulation levels. In some embodiments, the target frequency and duty cycle achieved are for a given titration session with an intermediate hold. In this case, the patient would visit a health care provider or physician for an evaluation. The physician would then release the hold on the titration processes, or initiate the beginning of therapy.

In some embodiments, in step 604, instead of reducing the frequency in order to facilitate increase of the output current, the pulse width may be reduced. For example, embodiments where the target pulse width is 250 μsec, the pulse width may be reduced, e.g., to 150 μsec or less. Then, the method proceeds to step 605, in which the output current is gradually increased again at the reduced pulse width level until the stimulation results in an intolerable side effect level or the target output current (e.g., 2.5 mA) is reached.

Therapy can also be autonomously titrated by the neurostimulator 12 in which titration progressively occurs in a self-paced, self-monitored fashion. The progression of titration sessions may occur on an autonomous schedule or may be initiated upon receipt of an input from the patient. Ordinarily, the patient 10 is expected to visit his healthcare provider to have the stimulation parameters stored by the neurostimulator 12 in the recordable memory 29 reprogrammed using an external programmer. Alternatively, the neurostimulator 12 can be programmed to automatically titrate therapy by up titrating the VNS through periodic incremental increases using titration sessions as described above. The titration process 600 will continue until the ultimate therapeutic goal is reached.

Following the titration period, therapeutic VNS, as parametrically defined by the maintenance dose operating mode, is delivered to at least one of the vagus nerves. The stimulation system 11 delivers electrical therapeutic stimulation to the cervical vagus nerve of a patient 10 in a manner that results in creation and propagation (in both afferent and efferent directions) of action potentials within neuronal fibers of either the left or right vagus nerve independent of cardiac cycle.

Figure 7A:
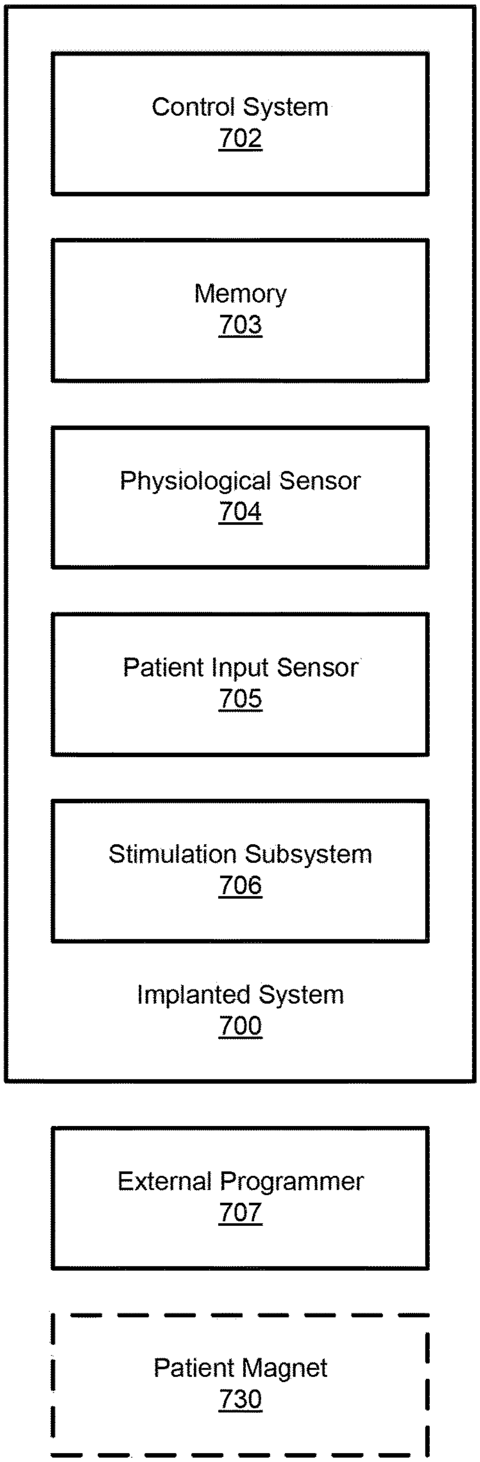
FIGS. 7A and 7B are block diagrams of neurostimulation systems, according to an exemplary embodiment.

FIG. 7A is a simplified block diagram of an implanted neurostimulation system 700, according to an exemplary embodiment. The implanted neurostimulation system 700 comprises a control system 702 comprising a processor programmed to operate the system 700, a memory 703, an optional physiological sensor 704, and a stimulation subsystem 706. The physiological sensor 704 may be configured to monitor any of a variety of patient physiological signals and the stimulation subsystem 706 may be configured to deliver a stimulation signal to the patient. In one example, the physiological sensor 704 comprises an ECG sensor or an accelerometer for monitoring heart rate and the stimulation subsystem 706 comprises a neurostimulator 12 programmed to deliver ON-OFF cycles of stimulation to the patient's vagus nerve. The implanted system 700 may include a patient input sensor 705, described in more detail below.

The control system 702 is programmed to activate the neurostimulator 12 to deliver stimulation signals at varying stimulation intensities to the patient and to monitor the physiological signals in response to those delivered stimulation signals.

The external programmer 707 shown in FIG. 7A may be utilized by a clinician or by the patient for communicating with the implanted system 700 to adjust parameters, activate therapy, retrieve data collected by the system 700 or provide other input to the system 700. In some embodiments, the external programmer 707 may be used remote from the implanted system 700 (e.g., when the patient is not at a clinic). For example, instead of the patient coming into the clinic for a check-up during a titration hold, the clinician may check on the patient remotely (e.g., phone call, video call, etc.). The clinician could then use the external programmer 707 to activate the next titration session, or modify parameters of the titration. In some embodiments, the external programmer 707 may provide an alert indicating the patient has reached a titration hold. In some embodiments, the patient receives an alert indicating a titration hold has been reached (e.g., email, text message, etc.). In some such embodiments, the external programmer 707 may include communication circuitry adapted to communicate over a long distance using one or more protocols (e.g., cellular, Internet, etc.). In some embodiments, the external programmer 707 may be configured to program the implanted system 700 with a prescribed time or window of time during which titration sessions may be initiated. This can be used to prevent a titration session from occurring at night when the patient's sleep is likely to be disturbed by the increase in stimulation intensity and resulting side effects.

Patient inputs to the implanted system 700 may be provided in a variety of ways. The implanted system 700 may include a patient input sensor 705. As described above, a patient magnet 730 may be used to provide external input to the system 700. When the patient magnet 730 is placed on the patient's chest in close proximity to the implanted system 700, the patient input sensor 705 will detect the presence of the magnetic field generated by the patient magnet 730 and provide a control input to the control system 702. The system 700 may be programmed to receive patient inputs to set the time of day during which titration sessions are to be initiated.

In other embodiments, the patient input sensor 705 may comprise a motion sensor, such as an accelerometer, which is configured to detect tapping on the surface of the patient's chest. The patient may use finger taps in one or more predetermined patterns to provide control inputs to the implanted system 700. For example, when the motion sensor detects three rapid taps to the patient's chest, that may trigger an operation on the implanted system 700 (e.g., to initiate a titration session). Alternatively, if the motion sensor detects a predetermined pattern of taps during a titration session, the implanted system 700 will interpret those taps as a patient input indicating that the patient's tolerance zone boundary has been exceeded.

In other embodiments, the patient input sensor 705 may comprise an acoustic transducer or other sensor configured to detect acoustic signals. The system 700 may be programmed to interpret the detection of certain sounds as patient inputs. For example, the patient may utilize an electronic device, such as a smartphone or other portable audio device, to generate one or more predetermined sequences of tones. The system 700 may be programmed to interpret each of these sequences of tones as a different patient input.

Figure 7B:
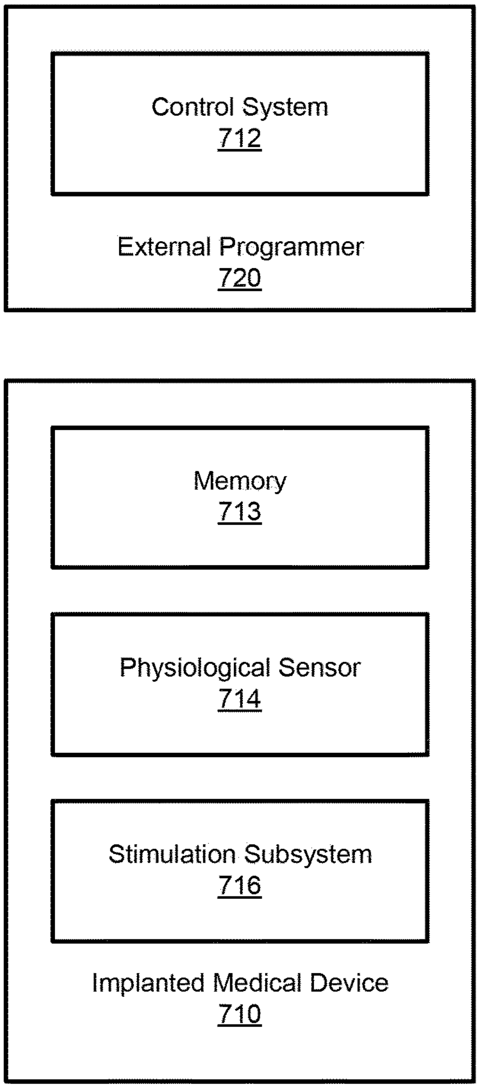

The titration of the stimulation signal delivery and the monitoring of the patient's physiological response (e.g., heart rate) may be advantageously implemented using a control system 702 in communication with both the stimulation subsystem 706 and the physiological sensor 704, such as by incorporating all of these components into a single implantable device 700. In accordance with other embodiments, an external control system 712 may be implemented in a separate implanted device or in an external programmer 720 or other external device, as shown in FIG. 7B to provide control over and communication with an implanted physiological sensor 714 and a stimulation subsystem 716 similar to those describe with regard to FIG. 6A. The external programmer 720 in FIG. 7B may be utilized by a clinician or by the patient for adjusting stimulation parameters. The external programmer 720 may be in wireless communication with the implanted medical device 710, which includes the stimulation subsystem 716 and a memory 713. In the illustrated embodiment, the physiological sensor 714 is incorporated into the implanted medical device 710, but in other embodiments, the sensor 714 may be incorporated into a separate implanted device, may be provided externally and in communication with the external programmer 720, or may be provided as part of the external programmer 720.

In various embodiments, a heart rate variability analysis may be used during the titration process to determine whether the VNS dose being applied to the patient is an effective dose. For example, a Poincaré analysis may be used during the titration process to verify that a VNS dose is an effective dose. In the cardiac stimulation context, performing a Poincaré analysis first includes measuring an interval between two successive R-waves (an "R-R interval"). As an illustration, R-R intervals are calculated as the time between successive QRS intervals in milliseconds. Each R-R interval (e.g., represented as $R_n(s)$) is then plotted against the successive R-R interval (e.g., represented as $R_{n+1}(s)$) to produce a scattergram termed a "Poincaré plot." The process of using a Poincaré analysis to determine whether an applied VNS dose in an effective dose is described in I. Libbus et al., "Quantitative Evaluation of Heartbeat Interval Time Series Using Poincaré Analysis Reveals Distinct Patterns of Heart Rate Dynamics During Cycles of Vagus Nerve Stimulation in Patients with Heart Failure," 50 J. of Electrocardiology 898-903 (2017), which is hereby incorporated by reference in its entirety.

Figure 8:
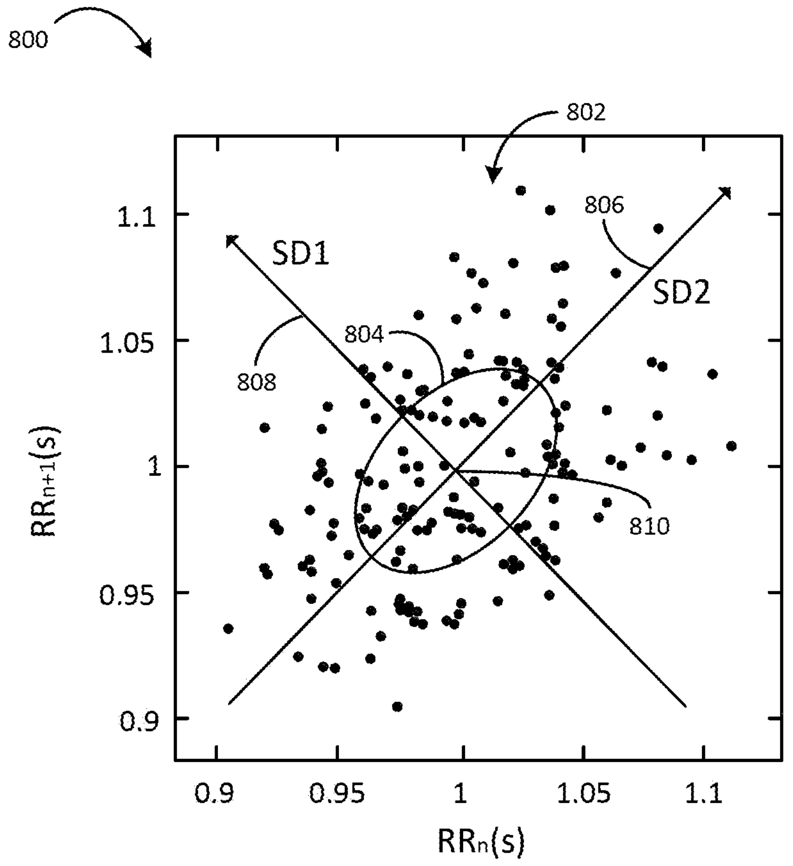
FIG. 8 is a diagram showing an example of a heart rate variability plot, according to an exemplary embodiment.

An example of a heart rate variability plot is shown in FIG. 8. Specifically, FIG. 8 illustrates a Poincaré plot 800. As shown in FIG. 8, the Poincaré plot 800 includes a number of points 802 produced by measuring the $RR_n(s)$ and the $RR_{n+1}(s)$ and plotting the $RR_n(s)$ versus the $RR_{n+1}(s)$. Once the Poincaré plot 800 has been created, standard deviations for the plot 800 may be determined. For example, an ellipse 804 may be fitted to the plot 800, with the center of the ellipse 804 coinciding with the center of the distribution of the points 802. An identity line 806 and a line perpendicular to the identity line 808 may then be plotted through the ellipse 804. Next, the standard deviation of points along the axis of the line perpendicular to the identity line 808 may be calculated (termed here as "SD1"), the standard deviation of points along the axis of the identity line 806 (termed here as "SD2") may be calculated. SD1 and SD2 are useful as measures of heart rate variability. More specifically, SD1 depicts the instantaneous beat-to-beat variability of the data, and SD2 provides a quantification of continuous long-term R-R intervals. The identity line 806 and the line perpendicular to the identity line 808 overlap at a centroid 810 of the ellipse 804, which represents the average heart rate.

Figure 9:
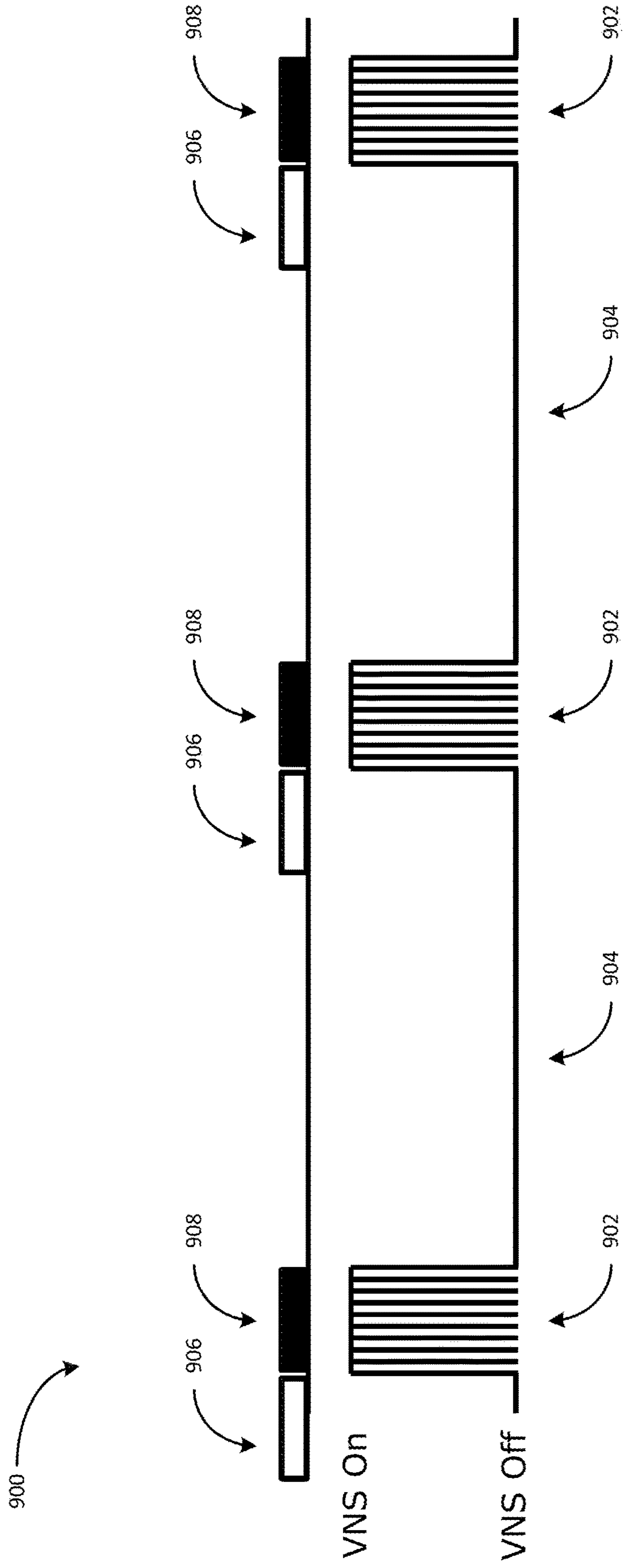
FIG. 9 is a diagram showing timing of an example of a heart rate variability analysis with respect to the timing of VNS stimulation, according to an exemplary embodiment.

A heart rate variability analysis may be used to determine whether an effective dose of VNS stimulation is being applied to a patient because effective stimulation may alter the patient's heart rate variability in observable ways. As an example, a Poincaré analysis may be used to determine whether an effective dose of VNS stimulation is being applied to a patient because if the patient is responding to the VNS stimulation, the centroid of the Poincaré plot will move up and to the right. Further, the SD1 of the Poincaré plot will increase in response to effective VNS stimulation. Accordingly, FIG. 9 illustrates a diagram 900 showing an example timing of a heart rate variability analysis, specifically a Poincaré analysis, with respect to the timing of VNS stimulation. As shown in FIG. 9, the VNS stimulation is applied according to a duty cycle with an ON period 902 (e.g., during which a VNS dose is applied to the patient) and an OFF period 904 (e.g., during which the VNS dose is suspended). For example, the ON period 902 may be 14 seconds, and the OFF period 904 may be 66 seconds. Accordingly, a baseline period 906 for the Poincaré analysis may be determined for at least a portion of the OFF period 904, and a stimulation period 908 for the Poincaré analysis may be determined for at least a portion of the ON period 902. For example, the baseline period 906 may be determined for the five seconds immediately preceding the VNS dose onset, and the stimulation period 908 may be determined during the last five seconds of VNS stimulation on-time.

Figure 10:
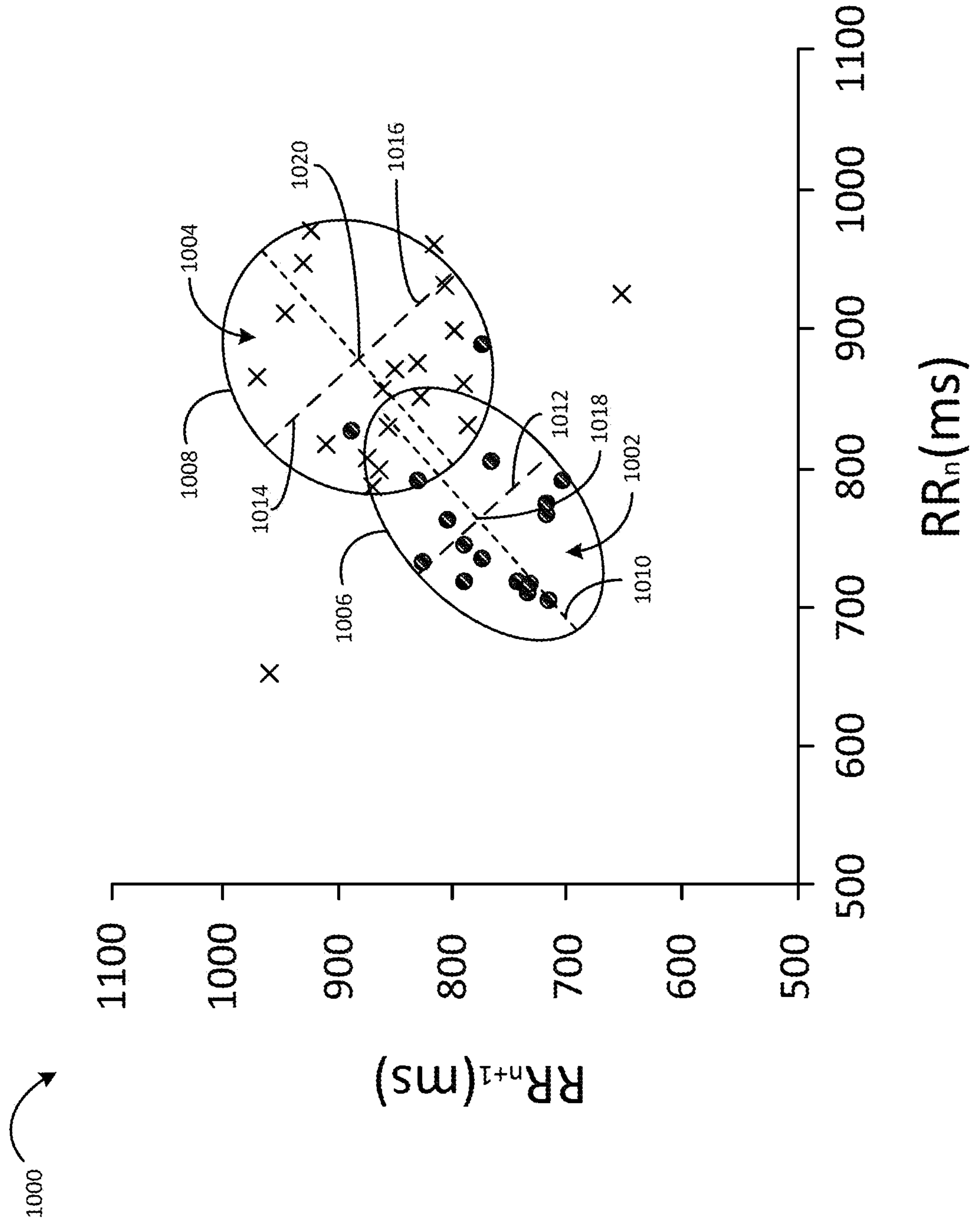
FIG. 10 is a diagram showing another example of a heart rate variability plot, according to an exemplary embodiment.

By taking heart rate variability measurements during VNS ON periods and VNS OFF periods, the effect of a VNS dose on heart rate variability may be measured or observed. For example, a Poincaré plot may be produced for the baseline period 906 and the stimulation period 908. As an illustration of how the effect of a VNS dose on heart rate variability may be observed, FIG. 10 shows an example plot, specifically an example Poincaré plot 1000, showing points 1002 from the baseline period 906 (e.g., plotted from the R-R intervals measured during the baseline period 906) and points 1004 from the stimulation period 908 (e.g., plotted from the R-R intervals measured during the stimulation period 908). As further shown in FIG. 10, an ellipse 1006 may be fitted to the baseline period points 1002, and an ellipse 1008 may be fitted to the stimulation period points 1004. An identity line 1010 and a line perpendicular to the identity line 1012 may be plotted through the ellipse 1006 of the baseline period points 1002, and the SD1 and SD2 may be calculated for the baseline period points 1002. Similarly, an identity line 1014 and a line perpendicular to the identity line 1016 may be plotted through the ellipse 1008 of the stimulation period points 1004, and the SD1 and SD2 may be calculated for the stimulation period points 1004. As shown in FIG. 10, the VNS stimulation is being applied at an effective dose, as the stimulation period points 1004 have migrated upward and to the right relative to the baseline period points 1002. This is particularly illustrated by a centroid 1018 of the baseline period points 1002 relative to a centroid 1020 of the stimulation period points 1004.

If, however, the VNS stimulation is not being applied at an effective dose, the stimulation period points 1004 will remain in the same location or substantially the same location as the baseline period points 1002. This may signal that the dose of VNS stimulation being applied to a patient is too low and that the intensity of the dose needs to be increased in order to deliver an effective dose to the patient. For example, a physician may increase the stimulation current amplitude of the dose, or the neurostimulator 12 may automatically increase the stimulation current amplitude of the dose, in response to a Poincaré plot showing little or no movement between the stimulation period points 1004 relative to the baseline period points 1002. Alternatively, the fact that VNS stimulation is not being applied at an effective dose may be demonstrated by the SD1 of the stimulation period points 1004 remaining the same or substantially the same as the SD1 of the baseline period points 1002. Accordingly, an increased VNS dose may be based on little to no increase in the SD1 of the stimulation period points 1004 compared to the baseline period points 1002.

Figure 11:
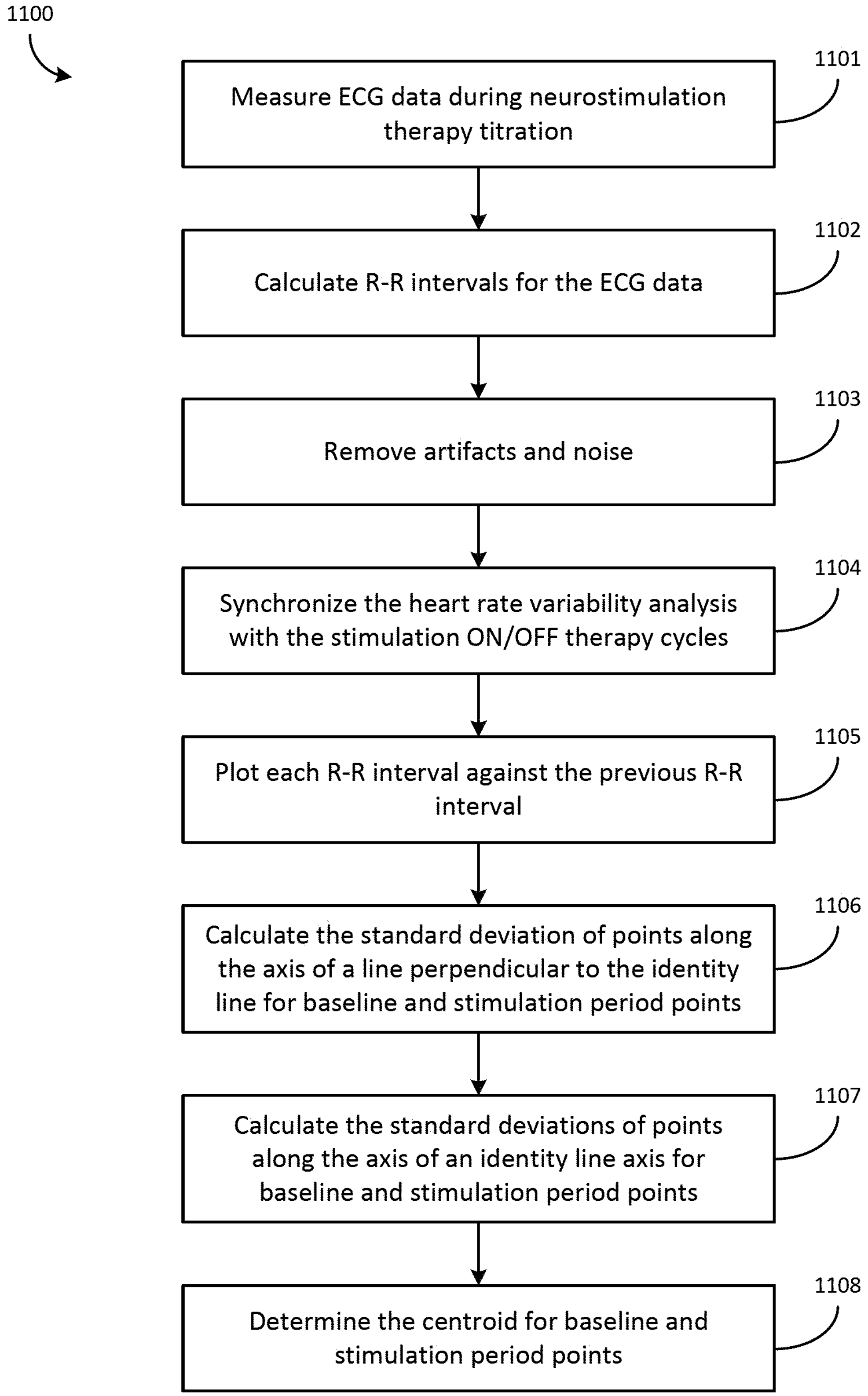
FIG. 11 is a flowchart of a process of using an example heart rate variability analysis during neurostimulation therapy titration, according to an exemplary embodiment.

FIG. 11 is a flow diagram showing an example method of using heart rate variability analysis during neurostimulation therapy titration. More particularly, FIG. 11 illustrate a method 1100 of using Poincaré analysis during neurostimulation therapy titration. At step 1101, the ECG of the patient is measured during neurostimulation therapy titration. For example, ECG data for the patient may be measured by the physiological sensor 704 of the implanted system 700 or by the physiological sensor 714 of the implanted medical device 710. At step 1102, the R-R intervals of the ECG data are calculated. At step 1103, artifacts and noise are removed from the data used for the Poincaré analysis. For example, a physician may manually determine outliers in the R-R intervals used in the Poincaré analysis. As another example, artifacts and noise may be automatically filtered from the ECG data used for the Poincaré analysis.

At step 1104, the analysis is synchronized with the stimulation ON/OFF therapy cycles. As an example, the Poincaré analysis is synchronized with the ON periods and OFF periods of the VNS duty cycles, as shown in FIG. 9. Each R-R interval is characterized as occurring during the VNS ON period or during the VNS OFF period. Accordingly, the ECG for the patient is sampled during at least a portion of the OFF period to produce a baseline period data set and sampled during at least a portion of the ON period to produce a stimulation period data set. At step 1105, each R-R interval is plotted against the previous R-R interval to create a Poincaré plot. Because the ECG data was sampled for baseline and stimulation periods in step 1104, the Poincaré plot includes both baseline period points and stimulation period points, as shown in FIG. 10.

At step 1106, the standard deviation of points along the axis of a line perpendicular to identity line (SD1) is calculated for the baseline period points and the stimulation period points. Likewise, at step 1107, the standard deviation of points along the axis of an identity line axis (SD2) is calculated for the baseline period points and the stimulation period points. As an example, an ellipse is fitted to each of the baseline period points and the stimulation period points, with the center of each ellipse coinciding with the center of the distribution of respective set of points. The SD1 for each set of points is calculated based on the axis of the line perpendicular to the identity line for each ellipse, and the SD2 for each set of points is calculated based on the axis of the identity line for each ellipse. Additionally, at step 1108, the centroid is determined for the baseline period points and the stimulation period points. For example, the centroid is determined to be the intersection point for the identity line and the line perpendicular to the identity line for each ellipse.

Figure 3:
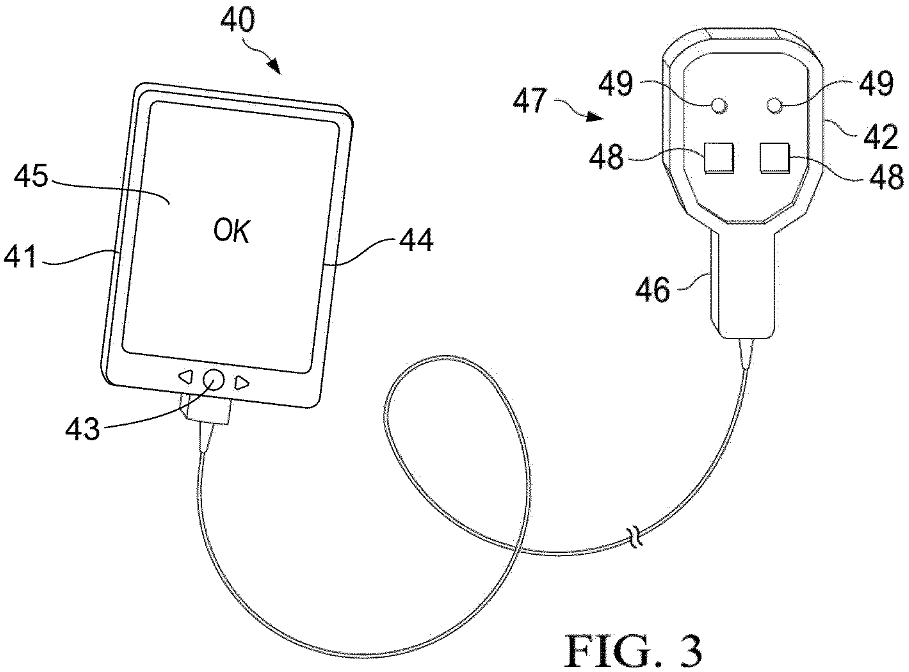
FIG. 3 is a diagram showing an external programmer for use with the implantable neurostimulator of FIG. 1, according to an exemplary embodiment.

In some arrangements, the heart rate variability analysis, such as a Poincaré analysis, is performed by an external programmer, such as the programming computer 41 shown in FIG. 3, the external programmer 707 shown in FIG. 7A, or the external programmer 720 shown in FIG. 7B. In the various examples described herein, the neurostimulation system is the implanted neurostimulation system 700 shown in FIG. 7A. However, it should be understood that a heart rate variability analysis may be performed by the neurostimulator 12 and/or the programming computer 41, by the implanted medical device 710 and/or the external programmer 720, or by any other implantable medical device and/or external programmer configured for VNS. Accordingly, in one example embodiment, in response to a signal from the external programmer 707, the physiological sensor 704 measures ECG data for the patient and transmits the ECG data back to the external programmer 707. The external programmer 707 calculates the patient's R-R intervals from the ECG data, creates a Poincaré plot (e.g., including the SD1, SD2, and centroid for each of the baseline period points and stimulation period points), and displays the Poincaré plot to a physician. Additionally, in some implementations, the display of the external programmer 707 may include coding in which the heartbeats measured during VNS ON periods are represented with different colors and/or symbols than the heartbeats measured during VNS OFF periods. The physician can then determine, based on the Poincaré plot, whether an effective dose of VNS stimulation is being delivered to the patient by the implanted system 700. Additionally, the physiological sensor 704 may measure and transmit the patient's ECG data in real-time such that the physician can increase or decrease the VNS dose delivered to the patient (e.g., by sending a command to the control system 702 by the external programmer 707) and monitor in real-time whether the increased or decreased VNS dose affects the heart rate variability (e.g., as demonstrated by a Poincaré plot) for the patient.

Additionally or alternatively, the physiological sensor 704 may measure historic ECG data for the patient (e.g., at predetermined intervals, such as for five minutes once a day). In response to an interrogation request from the external programmer 707, the implanted system 700 may transmit the historic ECG data to the external programmer 707. The external programmer 707 may then perform heart rate variability analyses, such as by creating Poincaré plots, for the patient using the patient's historic ECG data such that the physician may see, e.g., how the patient's heart rate variability has changed over time.

Moreover, in another embodiment, in addition to or rather than displaying heart rate variability information, such as Poincaré plots, to the physician, the external programmer 707 may perform an automatic heart rate variability analysis of the ECG data and provide recommendations to the physician. For example, in response to an instruction from the physician, the external programmer 707 may calculate the R-R intervals of the ECG data received from the implanted system 700, create a Poincaré plot for the ECG data, calculate the SD1 and SD2 for baseline period points and stimulation period points, and determine the centroids of baseline period points and the stimulation period points. The external programmer 707 may then use the SD1, SD2, and centroid for each of the baseline period points and stimulation period points to determine whether the patient's heart rate variability and/or average heart rate is different during stimulation periods as opposed to baseline periods and alert the physician of the results of the analysis. Further, if the patient's heart rate variability and/or average heart rate is not different during stimulation periods as opposed to baseline periods, the external programmer 707 may recommend a VNS dose adjustment to the physician (e.g., recommend that the physician increase the stimulation current intensity by a certain amount). For example, a distance between the centroid of the stimulation period points and the centroid of the baseline period points is less than a certain threshold value, the external programmer 707 recommends a VNS dose adjustment. As another example, if a difference between the SD1 of the stimulation period points and the SD1 of the baseline period points is less than a certain threshold value, the external programmer 707 recommends a VNS dose adjustment.

In other arrangements, the heart rate variability analysis is performed by the implantable neurostimulation system, such as the neurostimulator 12 shown in FIG. 1, the implanted system 700 shown in FIG. 7A, or the implanted medical device 710 shown in FIG. 7B. In one example embodiment, in response to a signal from the external programmer 707, the physiological sensor 704 measures the patient's ECG data, and the control system 702 creates Poincaré plots for the patient using the ECG data. The implanted system 700 then transmits the plots to the external programmer 707 such that the external programmer 707 may, e.g., display the plots to the physician and/or determine adjustments to the VNS dose as described above. The physiological sensor 704 may measure ECG data in real-time and/or historic ECG data for the patient, and the control system 702 may accordingly perform real-time and/or historic heart rate variability analysis, such as by creating Poincaré plots, for the patient.

In another embodiment, the implanted system 700 does not perform the heart rate variability analysis in response to a signal from the external programmer 707. Rather, the implanted system 700 performs the heart rate variability analysis in response to an event. In one example, after a certain time has elapsed since the VNS dose intensity was increased as part of the titration process, the physiological sensor 704 measures the patient's ECG data, and the control system 702 creates Poincaré plots for the patient using the ECG data. Using the Poincaré plots, the control system 702 then determines whether the increased VNS dose causes the centroid of the stimulation pulse points to migrate upward and to the right and/or causes an increase in the SD1 of the stimulation pulse points when applied. If the VNS dose does not cause a change in the centroid and/or the SD1, the control system 702 notifies the physician (e.g., by sending the external programmer 707 an alert over a network, by sending the alert to a computing system associated with the physician over a network, by sending the alert to a local telemetry device that provides the alert to the external programmer 707, etc.). The physician may then contact the patient to set up an appointment to check the current status of the VNS being applied to the patient, modify the VNS dose remotely (e.g., via the external programmer 707 communicating with the implanted system 700 over a network), and so on. Alternatively, or additionally, the control system 702 may automatically modify the VNS dose in response to determining that the VNS dose has not caused a change in the centroid and/or SD1 by a certain threshold value (e.g., the control system 702 may cause the stimulation subsystem 700 to increase the VNS dose to the next intensity level in the titration schedule).

In other embodiments, rather than performing the heart rate variability analysis in response to an event such as the next step in the titration schedule, the implanted system 700 performs the heart rate variability analysis periodically, such as once per day at a specified time, once per month at a specified time, and so on. Additionally, in some embodiments, the implanted system 700 may only perform the heart rate variability analysis once the titration schedule has been completed. The heart rate variability analysis is accordingly used to verify that the VNS stimulation is now at an effective dose and/or to verify that the VNS stimulation continues to be an effective dose.

In still another arrangements, the implantable neurostimulation system, such as the neurostimulator 12 shown in FIG. 1, the implanted system 700 shown in FIG. 7A, or the implanted medical device 710 shown in FIG. 7B, may communicate with a local telemetry device to perform the heart rate analysis. In one example embodiment, the physiological sensor 704 measures the patient's ECG data and provides the ECG data to a local telemetry device (e.g., transmits the ECG data via Bluetooth or RFID to a telemetry device located in the patient's home). For example, the physiological sensor 704 may measure and transmit the patient's ECG data every night when the patient is likely to be close to the local telemetry device. The telemetry device then creates Poincaré plots using the ECG and determines whether the current VNS dose causes the centroid of the stimulation pulse points to migrate upward and to the right and/or causes an increase in the SD1 of the stimulation pulse points when applied. If the VNS dose does not cause a change in the centroid and/or SD1 (e.g., by a certain threshold value), the telemetry device may send an alert to the physician (e.g., by sending an alert to the external programmer 707 or a computing system associated with the physician). The physician may then contact the patient to set up an appointment to check the current status of the VNS being applied to the patient, modify the VNS dose remotely (e.g., via the external programmer 707 communicating with the implanted system 700 over a network), and so on. Alternatively, the telemetry device may communicate with the implanted system 700 to modify the VNS dose (e.g., by sending a command to the control system 702 to increase the VNS dose).

In another embodiment, the implanted system 700 may provide ECG data to the telemetry device periodically, and the telemetry device may compile periodic reports for the physician. For example, the implanted system 700 may provide daily ECG data to the telemetry device, and the telemetry device may perform heart rate analyses (e.g., Poincaré analyses) on the data to compile monthly reports on the effect that titration is having on the patient (e.g., including analyses on whether a final titrated VNS dose continues to be effective for the patient). The telemetry device then transmits these reports to the physician (e.g., emails the reports to the physician, transmits the reports to the external programmer 707 over a network, and so on).

Using heart rate variability analysis in the context of VNS titration provides various technical advantages. For example, using a Poincaré analysis may provide technical advantages to a VNS therapy system or therapy monitoring system. Advantageously, as described herein, a Poincaré analysis may be used to show whether a given VNS dose is effective for a patient. Still, the Poincaré analysis is a computationally simple approach and thus performing a Poincaré analysis does not require much battery or processing power from a device. As such, a device (e.g., an external programmer, an implantable neurostimulator, etc.) may determine whether a VNS dose is effective for a patient, while minimizing battery consumption and processing power, by performing a Poincaré analysis for the patient. In turn, battery and processing power are preserved for other functions of the device, which improves the functioning of the device. As an illustration, the Poincaré analysis may be performed for a patient by an implantable neurostimulator delivering a VNS dose to the patient, to verify that the VNS dose is effective, without placing strains on the limited battery power of the implantable neurostimulator.

While embodiments been particularly shown and described, those skilled in the art will understand that the foregoing and other changes in form and detail may be made therein without departing from the spirit and scope. For example, in various embodiments described above, the stimulation is applied to the vagus nerve. Alternatively, spinal cord stimulation (SCS) may be used in place of or in addition to vagus nerve stimulation for the above-described therapies. SCS may utilize stimulating electrodes implanted in the epidural space, an electrical pulse generator implanted in the lower abdominal area or gluteal region, and conducting wires coupling the stimulating electrodes to the generator. Additionally, while the foregoing discussion focuses on heart rate variability analysis with respect to Poincaré analysis, it should be understood that other types of heart rate variability analysis are contemplated and may be used without departing from the spirit and scope of the present disclosure.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, Z, X and Y, X and Z, Y and Z, or X, Y, and Z. Thus, such conjunctive language is not generally intended to imply that certain embodiments require at least one of X, at least one of Y, and at least one of Z to each be present.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An implantable vagus nerve stimulation (VNS) system, comprising:

a sensor configured to measure a cardiac signal of a patient;

a stimulation subsystem configured to deliver VNS therapy to the patient; and a control system comprising a processor configured to:

monitor a heart rate variability of the patient using the cardiac signal;

deliver the VNS therapy to the patient at a first intensity;

determine that the heart rate variability has not changed by an amount indicative of an activation of a vagus nerve of the patient in response to the VNS therapy being delivered at the first intensity; and increase the VNS therapy to a second intensity based on the determination that the heart rate variability has not changed by the amount indicative of the activation of the vagus nerve of the patient.

2. The implantable VNS system of claim 1, wherein increasing the VNS therapy to the second intensity is performed automatically in response to the determination that the heart rate variability has not changed by the amount indicative of the activation of the vagus nerve of the patient.

3. The implantable VNS system of claim 1, wherein the processor is further configured to:

in response to the determination that the heart rate variability has not changed by the amount indicative of the activation of the vagus nerve of the patient, provide a notification to an external device.

4. The implantable VNS system of claim 1, wherein determining that the heart rate variability has not changed by the amount indicative of the activation of the vagus nerve of the patient comprises:

determining a stimulation heart rate variability of the patient during a stimulation period of the VNS therapy in which stimulation is delivered to the patient;

determining a baseline heart rate variability of the patient during a baseline period of the VNS therapy in which no stimulation is delivered to the patient; and determining that a difference between the baseline heart rate variability and the stimulation heart rate variability is below a threshold value, wherein determining that the heart rate variability has not changed by the amount indicative of the activation of the vagus nerve of the patient is based on determining that the difference between the baseline heart rate variability and the stimulation heart rate variability is below the threshold value.

5. The implantable VNS system of claim 4, wherein the stimulation subsystem is configured to deliver the VNS therapy according to a duty cycle, and the stimulation period is an ON-period of the duty cycle and the baseline period is an OFF-period of the duty cycle.

6. The implantable VNS system of claim 4, wherein the cardiac signal is an ECG signal.

7. The implantable VNS system of claim 6, wherein monitoring the heart rate variability comprises performing a real-time heart rate variability analysis using the ECG signal by:

measuring R-R intervals between successive R-waves within the ECG signal measured during the stimulation period of the VNS therapy and the baseline period of the VNS therapy; and comparing the R-R intervals measured during the stimulation period to the R-R intervals measured during the baseline period.

8. A method of delivery vagus nerve stimulation (VNS) therapy to a patient, the method comprising:

monitoring, using a cardiac signal measured via a sensor of an implantable VNS system, a heart rate variability of the patient;

delivering, via a stimulation subsystem of the implantable VNS system, the VNS therapy to the patient at a first intensity;

determining that the heart rate variability has changed by less than a threshold amount indicative of an activation of a vagus nerve of the patient in response to the VNS therapy being delivered at the first intensity; and increasing the VNS therapy to a second intensity based on the determination that the heart rate variability has changed by less than the threshold amount indicative of the activation of the vagus nerve of the patient in response to the VNS therapy being delivered at the first intensity.

9. The method of claim 8, wherein increasing the VNS therapy to the second intensity is performed automatically in response to the determination that the heart rate variability has changed by less than the threshold amount indicative of the activation of the vagus nerve of the patient in response to the VNS therapy being delivered at the first intensity.

10. The method of claim 8, further comprising:

in response to the determination that the heart rate variability changed by less than the threshold amount indicative of the activation of the vagus nerve of the patient, providing a notification to an external device.

11. The method of claim 8, wherein determining that the heart rate variability has changed by less than the threshold amount indicative of the activation of the vagus nerve of the patient in response to the VNS therapy being delivered at the first intensity comprises:

determining a stimulation heart rate variability of the patient during a stimulation period of the VNS therapy in which stimulation is delivered to the patient;

determining a baseline heart rate variability of the patient during a baseline period of the VNS therapy in which no stimulation is delivered to the patient; and determining that a difference between the baseline heart rate variability and the stimulation heart rate variability is below the threshold amount, wherein determining that the heart rate variability has not changed by the amount indicative of the activation of the vagus nerve of the patient is based on determining that the difference between the baseline heart rate variability and the stimulation heart rate variability is below the threshold amount.

12. The method of claim 11, wherein the VNS therapy is delivered according to a duty cycle, and the stimulation period is an ON-period of the duty cycle and the baseline period is an OFF-period of the duty cycle.

13. The method of claim 11, wherein the cardiac signal is an ECG signal.

14. The method of claim 13, monitoring the heart rate variability comprises performing a real-time heart rate variability analysis using the ECG signal by:

measuring R-R intervals between successive R-waves within the ECG signal measured during the stimulation period of the VNS therapy and the baseline period of the VNS therapy; and comparing the R-R intervals measured during the stimulation period to the R-R intervals measured during the baseline period.

15. A vagus nerve stimulation (VNS) system, comprising:

a local telemetry device comprising a processor; and an implantable system, comprising:

a sensor configured to measure a cardiac signal of a patient and transmit the cardiac signal to the local telemetry device; and a stimulation subsystem configured to deliver VNS therapy to the patient, the stimulation subsystem;

wherein the processor of the local telemetry device is configured to:

receive the cardiac signal from the implantable system;

monitor a heart rate variability of the patient using the cardiac signal;

cause the implantable system to deliver the VNS therapy to the patient at a first intensity;

determine that the heart rate variability has not changed by an amount indicative of an activation of a vagus nerve of the patient in response to the VNS therapy being delivered at the first intensity; and cause the implantable system to increase the VNS therapy to a second intensity based on the determination that the heart rate variability has not changed by the amount indicative of the activation of the vagus nerve of the patient.

16. The VNS system of claim 15, wherein causing the implantable system to increase the VNS therapy to the second intensity is performed automatically in response to the determination that the heart rate variability has not changed by the amount indicative of the activation of the vagus nerve of the patient.

17. The VNS system of claim 15, wherein the processor is further configured to:

in response to the determination that the heart rate variability has not changed by the amount indicative of the activation of the vagus nerve of the patient, provide a notification to a computing system associated with a healthcare provider.

18. The VNS system of claim 15, wherein determining that the heart rate variability has not changed by the amount indicative of the activation of the vagus nerve of the patient comprises:

determining a stimulation heart rate variability of the patient during a stimulation period of the VNS therapy in which stimulation is delivered to the patient;

determining a baseline heart rate variability of the patient during a baseline period of the VNS therapy in which no stimulation is delivered to the patient; and determining that a difference between the baseline heart rate variability and the stimulation heart rate variability is below a threshold value, wherein determining that the heart rate variability has not changed by the amount indicative of the activation of the vagus nerve of the patient is based on determining that the difference between the baseline heart rate variability and the stimulation heart rate variability is below the threshold value.

19. The VNS system of claim 18, wherein the stimulation subsystem is configured to deliver the VNS therapy according to a duty cycle, and the stimulation period is an ON-period of the duty cycle and the baseline period is an OFF-period of the duty cycle.

20. The VNS system of claim 15, wherein the cardiac signal is an ECG signal.

* * * * *